US00PP35807P3

(12) United States Plant Patent
Chandra et al.

(10) Patent No.: US PP35,807 P3
(45) Date of Patent: May 14, 2024

(54) HYBRID ST. AUGUSTINEGRASS NAMED 'DALSA 1618'

(50) Latin Name: ***Stenotaphrum secundatum* interploid hybrid**
Varietal Denomination: DALSA 1618

(71) Applicant: The Texas A&M University System, College Station, TX (US)

(72) Inventors: Ambika Chandra, McKinney, TX (US); Anthony D. Genovesi, Dallas, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/892,784

(22) Filed: Aug. 22, 2022

(65) Prior Publication Data

US 2024/0065122 P1 Feb. 22, 2024

(51) Int. Cl.
*A01H 5/12* (2018.01)
*A01H 6/46* (2018.01)

(52) U.S. Cl.
USPC ..... Plt./392

(58) Field of Classification Search
USPC ..... Plt./392
CPC ... A01H 5/12; A01H 5/10; A01H 6/46; A01H 6/00
See application file for complete search history.

(56) References Cited

U.S. PATENT DOCUMENTS

PP4,097 P 9/1977 Gruis et al.
PP6,372 P * 11/1988 Mixson ..... Plt./392
PP6,922 P 7/1989 Mixson et al.
PP9,395 P 12/1995 Kirkland et al.
PP17,095 P2 9/2006 Riordan
PP21,280 P3 9/2010 Nagata et al.
PP27,393 P3 * 11/2016 Chandra ..... Plt./392
PP32,645 P3 12/2020 Kenworthy et al.

OTHER PUBLICATIONS

Amerishade retrieved on May 24, 2023 at https://tmsearch.uspto.gov/bin/showfield?f=doc&state=4803:5I44u0.4.1, 2 pp. (Year: 2023).*
Captiva retrieved on May 24, 2023 at https://tmsearch.uspto.gov/bin/showfield?f=doc&state=4803:5I44u0.5.2, 2 pp. (Year: 2023).*
Citrblue retrieved on May 24, 2023 at https://tmsearch.uspto.gov/bin/showfield?f=doc&state=4807:v4rxek.2.2, one page. (Year: 2023).*
Miracle-Gro retrieved on May 24, 2023 at https://tmsearch.uspto.gov/bin/showfield?f=doc&state=4809:ozwhxk.4.23, 2 pp. (Year: 2023).*
Osmocote retrieved on May 24, 2023 at https://tmsearch.uspto.gov/bin/showfield?f=doc&state=4810:845qxw.2.3, 2 pp. (Year: 2023).*
Palmetto retrieved on May 24, 2023 at https://tmsearch.uspto.gov/bin/showfield?f=doc&state=4803:5I44u0.3.3, one page. (Year: 2023).*
Tamstar retrieved on May 24, 2023 at https://tmsearch.uspto.gov/bin/showfield?f=doc&state=4809:ozwhxk.2.1, one page. (Year: 2023).*
YouTube Texas A&M Agrilife Extension Dalsa 1618 retrieved on May 24, 2023 at https://www.youtube.com/watch?v=WFREixLCMB4https://www.youtube.com/watch?v=WFREixLCMB4, 2 pp. (Year: 2023).*
Saldana. Texas A&M AgriLife Research's Cobalt St. Augustine ready for production. AgriLife Today. Dated Jan. 27, 2022, 5 pp.
SodSolutions Professionals. Introducing Cobalt™ Hybrid St. Augustinegrass. Accessed on Oct. 4, 2022, 11 pp.

* cited by examiner

*Primary Examiner* — June Hwu
(74) *Attorney, Agent, or Firm* — Dentons US LLP

(57) ABSTRACT

'DALSA 1618' is an interploid hybrid variety of St. Augustinegrass. 'DALSA 1618' possesses a unique combination of drought and shade tolerance that allows its use across the southcentral and southeastern United States.

12 Drawing Sheets

Latin name of the genus and species of the plant claimed: *Stenotaphrum secundatum* interploid hybrid.

Variety denomination: 'DALSA 1618'.

BACKGROUND OF THE INVENTION

St. Augustinegrass (*Stenotaphrum secundatum* (Walt.) Kuntze) is a warm-season turfgrass commonly planted in residential and commercial landscapes across the southern United States. Genetic variability in St. Augustinegrass is partitioned within and between ploidy levels. Diploids (2n=18) and polyploids (2n≥27) exhibit varying degrees of tolerance to abiotic stress such as drought, shade and cold, as well as resistances to insect pests and pathogens. With limited water during early stages of drought stress conditions, polyploids are less likely to wilt and enter dormancy as compared to diploids (Busey, 1996). 'Floratam', a polyploid cultivar, is still considered the most drought tolerant standard for St. Augustinegrass. Shade tolerance has generally been observed in diploids like 'Amerishade®' (also known as 'TR 6-10'; U.S. Plant Pat. No. 17,095) and 'DelMar' (U.S. Plant Pat. No. 6,372) while 'Floratam' (not patented) is shade sensitive. The ability to tolerate freezing temperatures is directly related to a plant's ability to acclimate to colder temperatures prior to exposure to freezing temperatures (Kimball et al., 2017). Diploid cultivars like 'Raleigh' (not patented) and 'Palmetto®' (also known as 'SS-100'; U.S. Plant Pat. No. 9,395), e.g., have superior cold tolerance whereas 'Amerishade®' (diploid) and 'Floratam' (polyploid) are more sensitive to winterkill due to a lack of cold acclimation. Although some diploid germplasm accessions have expressed pest resistance (Carbajal et al., 2020), polyploids like 'Floratam' generally demonstrate greater resistance than diploids to southern chinch bugs (*Blissus insularis* Barber) but have similar resistance to gray leaf spot (*Pyricularia grisea* Sacc.). Furthermore, diploids such as 'Amerishade®' with more diminutive or dwarf-like growth habits are slower to establish than polyploids like 'Floratam', though some diploids like 'Raleigh' and 'Palmetto®' exhibit faster establishment rate (Moseley et al., 2021). Dwarf cultivars are preferred by consumers for their tolerance to lower mowing heights and reduced mowing frequency.

Turfgrass breeders have primarily utilized genetic variability present within diploid St. Augustinegrass germplasm for new cultivar development. Sterility barriers and abnormal chromosome pairing between ploidy levels have hindered the extensive use of polyploid germplasm in making genetic improvements until embryo rescue technology was utilized to develop interploid (polyploid×diploid) (Genovesi et al., 2009 and 2017) and inter-specific hybrids of St. Augustinegrass with pembagrass (Genovesi et al., 2017). Interploid hybrids of St. Augustinegrass have been shown to exhibit enhanced turfgrass quality under extreme drought conditions and moderate shade environments (Chandra et al., 2015; Meeks and Chandra, 2019 and 2021). However, commercial viability of some of the interploid hybrids has been hindered due to issues related to sod tensile strength and harvestability. Thus, sod harvestability has become a strong focus for the future of St. Augustinegrass production of widely adaptable and desirable interploid hybrids. 'DALSA 1618', an interploid hybrid, was developed at Texas A&M AgriLife Research-Dallas and was evaluated in multiple environments across the southern U.S. to study it's biotic and abiotic stress tolerance, visual turfgrass quality characteristics, herbicide tolerance for weed management, and sod tensile strength.

SUMMARY OF THE INVENTION

The present disclosure relates to a new and distinct *Stenotaphrum secundatum* interploid hybrid variety named 'DALSA 1618'. 'DALSA 1618', formerly tested as 'TAES 5896-09' and 'TXSA-156', was produced in 2009 near Dallas, TX from a cross between 'TAES 5384' (female parent; unpatented) and 'Amerishade®' (male parent; U.S. Plant Pat. No. 17,095). 'TAES 5384' is an ancuploid (2n=2x=30, Milla-Lewis et al., 2013) exhibiting antibiosis to southern chinch bug (*Blissus insularis* Barber) and resistance to gray leaf spot disease (*Pyricularia grisea* Sacc.); and 'Amerishade®' is a dark green semi-dwarf diploid cultivar (2n=2x=18, Riordan, 2006) with tolerance to moderate shade densities. Due to ploidy differences and potential genetic incompatibility, embryos were rescued in vitro to produce a population of 756 interploid progeny. 'DALSA 1618' represents an individual interploid progeny from this population. 'DALSA 1618' was first asexually propagated in Dallas, Texas at the Texas A&M AgriLife Research Center via stolon propagation.

'DALSA 1618' is an interploid hybrid St. Augustinegrass that when compared to the polyploid, 'Floratam', has a similar leaf blade width and stolon thickness, but shorter leaf length and stolon internode length. The performance of 'DALSA 1618' varied depending on the geographic locations and environmental conditions. Overall, 'DALSA 1618' established faster than 'CitraBlue®' (also known as 'FSA 1602'; U.S. Plant Pat. No. 32,645) and similarly to other tested commercial cultivars. Along latitudes 32 and 33 and coastal locations, 'DALSA 1618' exhibited high turfgrass quality which was generally higher than 'Floratam'. In Ft. Lauderdale, FL, the quality ratings of 'DALSA 1618' was not as high as 'CitraBlue®' but maintained acceptable quality similar to other cultivars. When drought stressed, 'DALSA 1618' retains a darker green color and higher quality longer like the most drought tolerant cultivar, 'Floratam', such that it can tolerate reduced irrigation rate of once every two weeks when weekly irrigation is not available or restricted. Under the combined stressor of cold and shade, 'DALSA 1618' performed better than 'Floratam' which is both cold and shade sensitive. Under moderate shade, 'DALSA 1618' maintains its genetic color and high shoot density like shade tolerant diploid cultivars which contributes to its high turfgrass quality. The leaf elongation rate of 'DALSA 1618' is also like that of shade tolerant diploids 'Palmetto®' and 'Raleigh'. As an interploid hybrid, 'DALSA 1618' exhibited early greenup which was better than 'Floratam' and in most environments was like 'Raleigh'. Furthermore, 'DALSA 1618' expresses less cold sensitivity than 'Floratam' (not patented) and 'CitraBlue®' (a.k.a. 'FSA 1602'; U.S. Plant Pat. No. 32,645).

In summary, 'DALSA 1618' exhibits comparable establishment and drought resistance to 'Floratam' but with improved turfgrass quality, spring greenup, and cold and shade tolerances. 'DALSA 1618' has the same level of tolerance to large patch as other cultivars, but requires further testing. As for gray leaf spot, 'DALSA 1618' is like that of 'CitraBlue®' and either comparable to or better when compared to other tested cultivars. These combinations of traits are unique in a St. Augustinegrass cultivar, which should allow 'DALSA 1618' to succeed in multiple environments across the southern United States.

'DALSA 1618' turf can be distinguished from 'TAES 5384' (female) at least based upon their turf color. Specifically, 'DALSA 1618' exhibits a darker green leaf color as compared to its female parent 'TAES 5384'. 'DALSA 1618' turf can be distinguished from 'Amerishade®' (male parent) at least based upon their internode length and diameter. Specifically, 'DALSA 1618' exhibits longer stolon node and greater internode diameter as compared to its male parent 'Amerishade®'. Additionally, 'DALSA 1618' exhibits more stolon anthocyanin pigmentation as compared to its male parent 'Amerishade®'.

BRIEF DESCRIPTION OF THE DRAWINGS

'DALSA 1618' is illustrated by the accompanying photographs, which show the turf's vegetative and floral characteristics. The colors shown are as true as can be reasonably obtained by conventional photographic procedures.

DETAILED BOTANICAL DESCRIPTION

Figure 1:
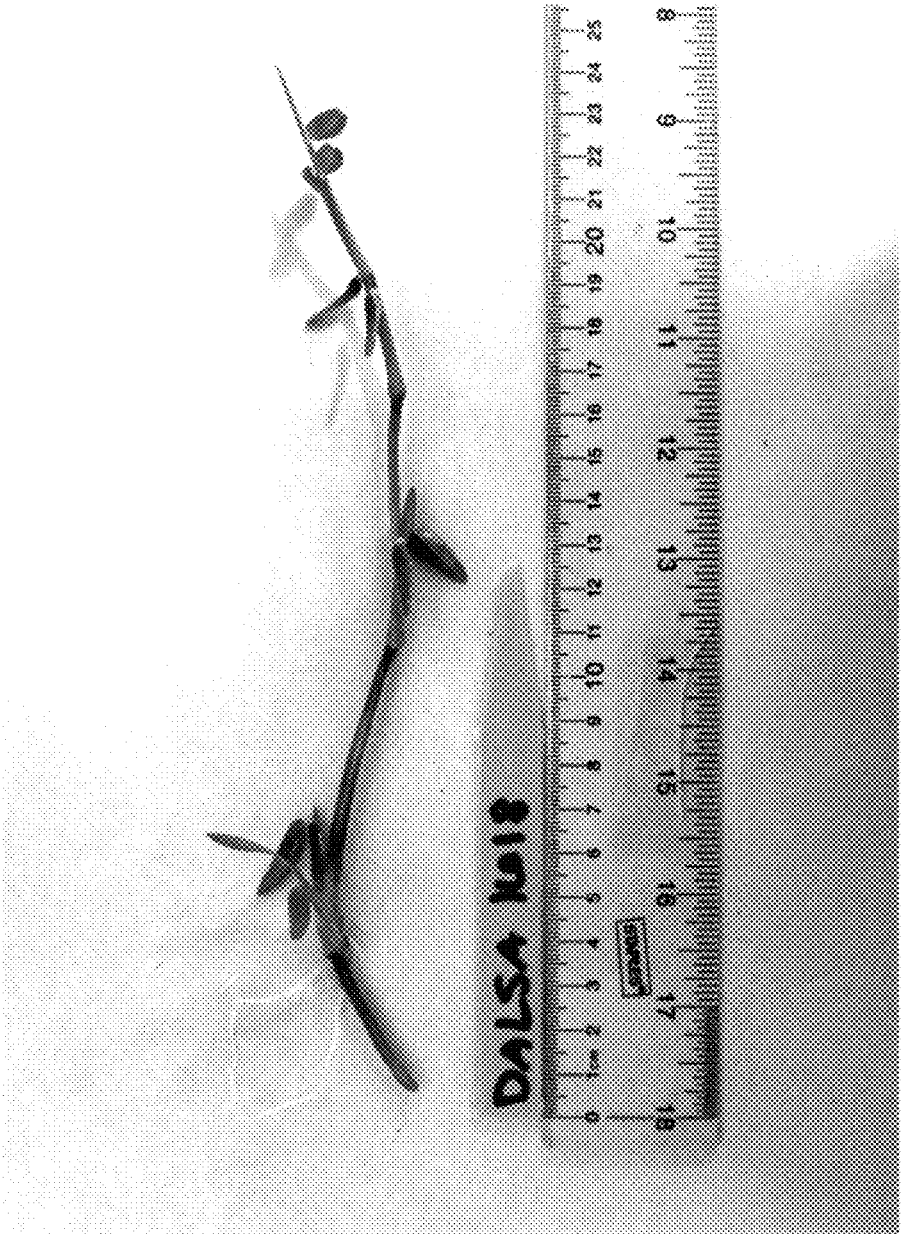
FIG. 1 Shows stolon and root development of 'DALSA 1618' after 7 days in water cups.

The following detailed description sets forth the distinctive characteristics of 'DALSA 1618'. Vegetative and floral data were collected in Dallas, TX from propagated material under greenhouse conditions. Color references are to the Munsell Color Chart; 1977 Edition of the Munsell Color Charts for Plant Tissues, unless otherwise indicated. Color designations provided refer to both mature and immature stages unless otherwise indicated. If any Munsell color designations below differ from the accompanying photographs, the Munsell color designations are accurate.

Plant:
- *Growth habit*.—Lateral growth by stolons.
- *Natural plant height* (*at maturity*).—Ranges from 20.5 to 45.8 cm, 39 cm on average.
- *Tillers on the culm*.—2 to 3.
- *Self-fertility*.—Fertile, produces 1 seed per spikelet.

Leaves:
- *Length* ($5^{th}$ *node*).—42.7 mm.
- *Width* ($5^{th}$ *node*).—6.0 mm.
- *Unmown leaf length*.—9.5 cm.
- *Length* (*flag leaf*).—Ranges from 2.2 to 4.1 cm, 3.1 cm on average.
- *Width* (*flag leaf*).—Ranges from 6 to 8 mm, 7.4 mm on average.
- *Leaf curling*.—Absent.
- *Leaf sheath pubescence*.—Absent.
- *Leaf sheath hairs on surface*.—Absent.
- *Leaf sheath hairs on margin*.—Absent.
- *Leaf sheath margin roughness* (*to touch*).—Rough.
- *Leaf sheath surface roughness* (*to touch*).—Smooth.
- *Leaf sheath hairs just beneath leaf blade* (*under collar*).—Present, approx. 1.16 mm length.
- *Leaf sheath color*.—7.5GY 7/5.
- *Leaf collar color*.—5GY 7/6.
- *Anthocyanin coloration of the basal leaf sheath*.—None.
- *Lower surface leaf coloration*.—7.5GY 8/6.
- *Upper surface leaf coloration*.—2.5G 5/4.
- *Auricles*.—Absent.
- *Ligules*.—Absent.
- *Ligule hairs*.—Absent.
- *Keel*.—Yes, towards the base of new leaves.
- *Leaf blade venation pattern*.—Parallel.
- *Leaf blade color* (*winter*).—Dormant straw-colored.
- *Leaf blade luster* (*upper side*).—Dull.
- *Leaf blade luster* (*lower side*).—Shiny.
- *Leaf blade hairs on margin*.—Absent.
- *Leaf blade hairs* (*upper side*).—Few.
- *Leaf blade hairs* (*lower side*).—Absent.

Stem color: 5Y 5/4.

Stolon nodes and internodes:
- $5^{th}$ *internode length*.—66.8 mm.
- $5^{th}$ *internode diameter* (*vertical*).—3.0 mm.
- $5^{th}$ *diameter* (*horizontal*).—10.1 mm.
- *Number of nodes within* 12 *inches*.—5.

Shoot color: 7.5 GY 4/3.

Ascending culm internode length: Ranges from 4.5 to 7 cm, 5.5 cm on average.

Culm node pubescence: Absent.

Time of flowering: May 15 (in Dallas, TX).

Glumes: 2.5GY 7/6 coloration when immature, straw-colored when mature, no anthocyanin coloration, elliptical in dorsal view.

Lemmas: 2.

Lemma shape: Ovoid.

Lemma length: 4.07 mm.

Lemma colors: 2.5 GY 8/4.

Palea shape: Ovoid.

Palea size: 3.7 mm.

Palea colors: 2.5 GY 8/4.

Bristles: Absent.

Ligule color: Absent.

Inflorescence:
- *Type*.—Spike-like raceme.
- *Shape of rachis*.—Flat.
- *Collar of the rachis*.—2.5 GY 6/6 coloration.

*Panicle description* (*habit; type*).—Produces 2 to 4 rachis per culm with one primary and several axillaries.

*Panicle length*.—Ranges from 19.4 to 24.2 cm, 21.6 cm on average.

*Panicle diameter*.—Ranges from 5 to 7 mm, 5.8 mm on average.

*Color*.—2.5G 5/4.

*Stigma length*.—2.5 mm.

*Stigma color*.—5RP 4/4.

*Stigma characterization*.—2 feathery stigmas per floret.

*Anther color* (*mature/dried*).—7.5 YR 6/10.

*Peduncle length*.—Ranges from 4.7 to 6.4 cm, 5.6 cm on average.

*Pedicel*.—All sessile (immobile); longest pedicel ranges from 1.99 to 3.28 mm, 2.8 mm on average.

*Pedicel color*.—5GY 7/4 and 5GY 5/8.

Awns: Absent.

Culm diameter: Ranges from 1.34 to 1.86 mm, 1.6 mm on average.

Number of panicles bearing tillers in the culm: All panicles have at least 1 axillary inflorescence.

Culm color: 2.5G 5/4.

Culm anthocyanin coloration of the nodes and internodes: 2.5 R 4/4.

Caryopsis shape: Ellipsoid.

Grain shape: Ellipsoid.

Spikelets per rachis: Ranges from 42 to 51, 46.6 on average.

Florets per spikelet: Two.

Environmental resistance:

*Cold* (*injury*).—Moderately Resistant.

*Heat*.—Moderately Resistant.

*Drought*.—Moderately Resistant.

*Low fertility*.—Moderately Resistant.

*Alkalinity* (*pH*>7.5).—Highly Resistant.

Figure 7:
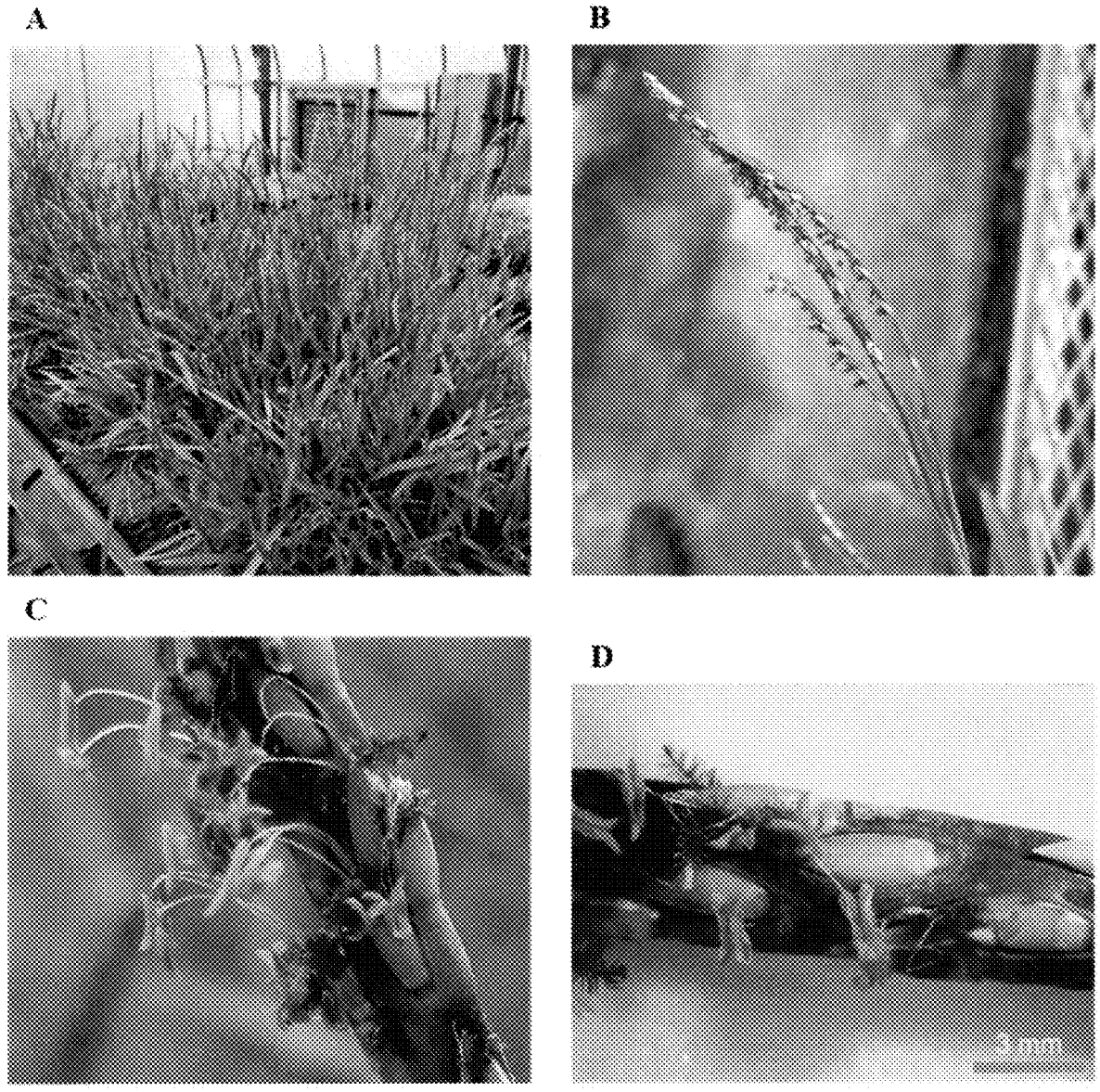
FIG. 7 Shows inflorescence production from four nine-month-old 'DALSA 1618' 5-gal pots grown in the greenhouse on May 21, 2021 (A); 'DALSA 1618' exhibiting one primary and two axillary rachis emerging from the same culm (B); spikelet grouping (pairs or triplets), spikelet pattern, stigma coloration, and immature and mature anther coloration, and anther number per spikelet (C and D).
Figure 8:
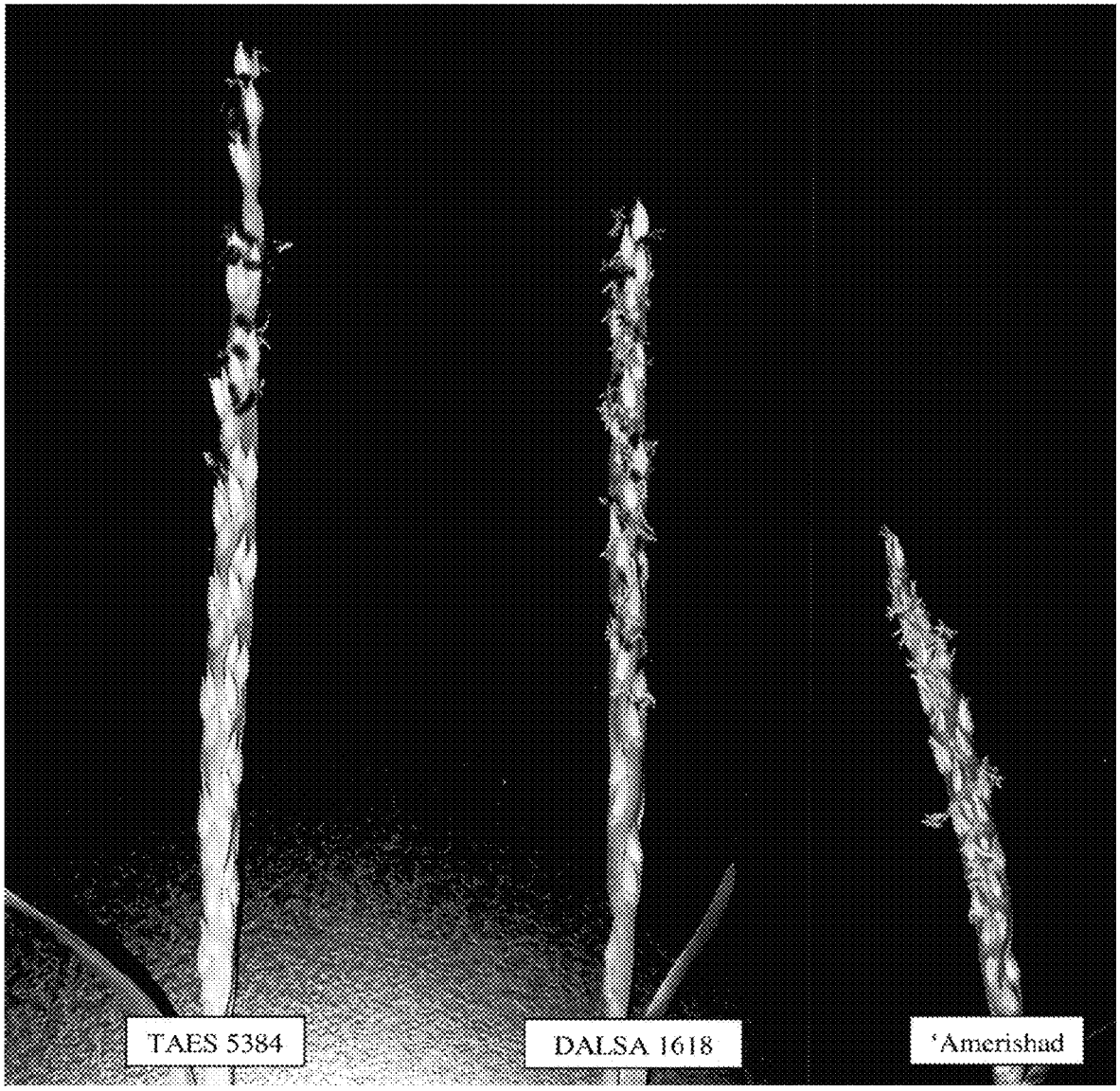
FIG. 8 Shows inflorescence characteristics of 'DALSA 1618' (middle), 'TAES 5384' (left), and 'Amerishade®' (right).

Floral characteristics 'DALSA 1618' was propagated into five-gallon pots in late August 2020, fertilized with 12-9-6 (N-P-K, Miracle-Gro® Liquifeed Bloom Booster), and maintained under greenhouse conditions (85°/65° F.). 'DALSA 1618' began flowering on Nov. 15, 2020 and had nearly completed flowering by May 21, 2021 when floral measurements were collected from the 12 tallest inflorescences (FIG. 7A). All floral measurements were recorded from the primary rachis on each of the tallest culms. Ascending culm plant height was measured from the base of the plant to the tip of the inflorescence. The ascending culm internode length as measured between the second and third nodes. Peduncle length was recorded from the base of the rachis to the flag leaf node. Panicle length is the total length between the flag leaf node and tip of the inflorescence. Panicle diameter was measured at the widest point across the flattened side of each inflorescence. Culm diameter was measured just below the rachis on the main stem. Pedicel length was measured from the $2^{nd}$ (middle) spikelet of a group of three spikelets, as it was most often the longest. The number of spikelets appearing on each of the primary inflorescences were visually counted. 'DALSA 1618' produces flat, thick, spike-like racemes often with two or three axillary/tillering rachis from the same culm, with most commonly a total of three (FIG. 7B). The average inflorescence height is 39 cm with an ascending culm internode length of 6 cm. Each inflorescence has a flag leaf with an average width of 7 mm and length of 3 cm. Peduncle length averages 6 cm. Panicle length and diameter are 22 cm and 6 cm, respectively. The rachis is brittle and 16 cm in length, on average. Embedded spikelets are ovoid in shape and occur on only one side of the rachis and are often paired or in triplets on alternating sides until ascending to the tip where they are grouped more densely (FIGS. 7C and 7D). Each rachis has an average of 47 spikelets that are anchored by sessile (immobile) pedicles 3 mm in length. Each spikelet has two florets. 'DALSA 1618' is self-fertile.

Figure 2:
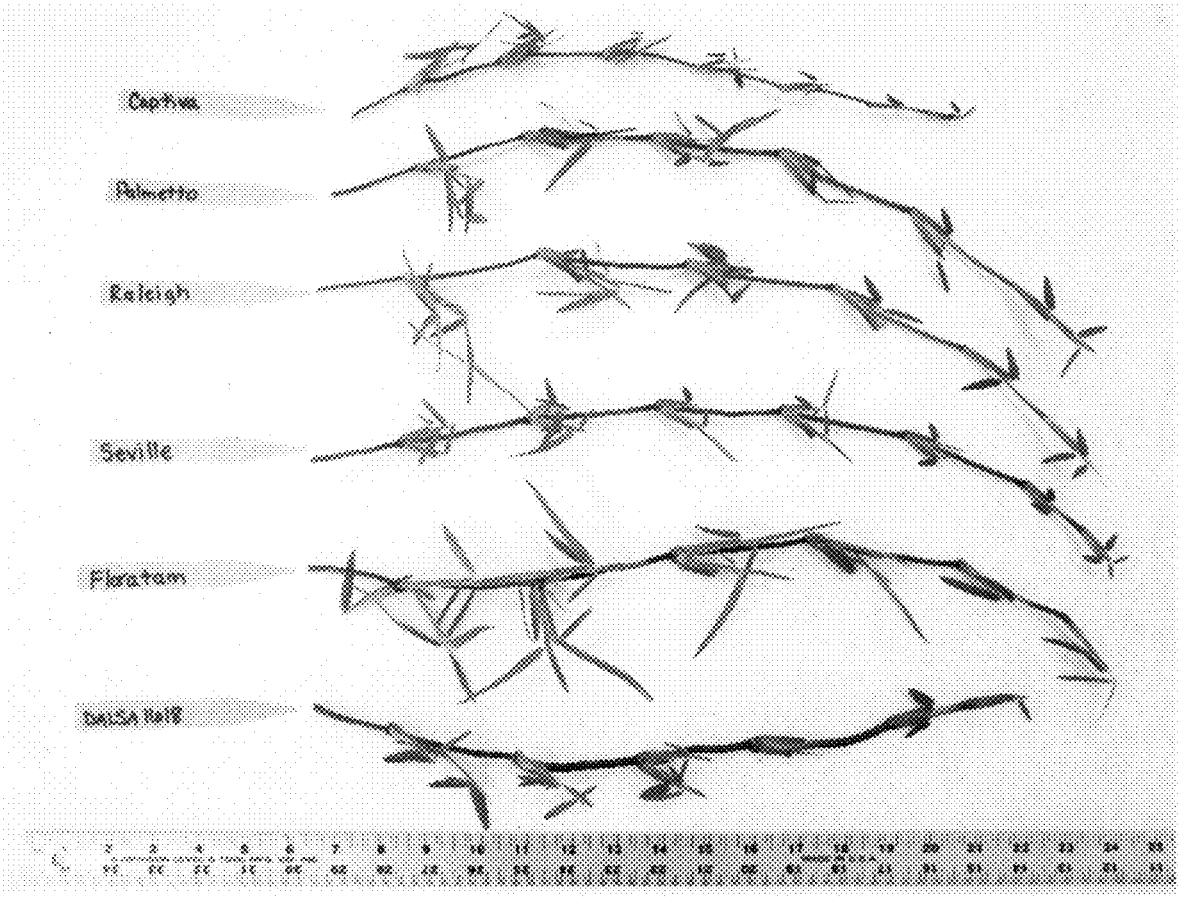
FIG. 2 Shows stolon characteristics of 'DALSA 1618' (bottom stolon) compared to five commercial cultivars. Photographed Mar. 16, 2020.

Morphological analysis of 'DALSA 1618': Experiments were conducted under greenhouse conditions for the purpose of comparing the morphology of 'DALSA 1618' to different sets of commercial cultivars. The plant material for the first experiment was propagated on Sep. 30, 2019. For each of 'DALSA 1618' and five cultivars ('Captiva®'(a.k.a 'NUF76'; U.S. Plant Pat. No. 21,280), 'Floratam', 'Palmetto®', 'Raleigh', and 'Seville' (U.S. Plant Pat. No. 4,097)), eight rooted stolons containing three nodes and an apical meristem were planted into each of two replicate 15.2 cm square pots filled with potting soil mixed with Osmocote® Classic slow-release fertilizer (14-14-14, ICL Specialty Fertilizers) at a rate of 5 $kg \cdot m^3$. Liquid rooting solution was applied weekly for the first two weeks followed by monthly applications of 24-8-16 (N-P-K, Miracle-Gro®, Scotts Company, Inc.) at 3.3 g·L. Pots were trimmed every two weeks to encourage establishment. Trimming was suspended on 30 Jan. 2020. After 43 days, morphological measurements were recorded on Mar. 13, 2020. The leaf length of 'DALSA 1618' (42.7 mm) emerging from the $5^{th}$ node is like 'Raleigh', shorter than 'Floratam', but longer than 'Palmetto®', 'Captiva®', and 'Seville' (Table 1). However, the leaf width (6.0 mm) is like the polyploid cultivar, 'Floratam', which is wider than the diploid cultivars, 'Captiva®', 'Palmetto®', 'Raleigh', and 'Seville'. The internode length between the $5^{th}$ and $6^{th}$ nodes for 'DALSA 1618' (66.8 mm) is shorter than 'Floratam' and 'Raleigh', but longer than 'Palmetto®', 'Seville', and 'Captiva®'. Internode and node diameters of 'DALSA 1618' (3.0 mm and 10.1 mm, respectively) are like 'Floratam', which is thicker than other tested cultivars. The average number of nodes within 30.5 cm for 'DALSA 1618' (5.0) is like 'Palmetto®', which is fewer than 'Captiva®' and 'Seville', but more than 'Raleigh' and 'Floratam' (FIG. 2). Unmown leaf lengths for 'DALSA 1618' (9.5 cm) are like 'Captiva®', 'Palmetto®', and 'Raleigh', which is shorter than 'Seville' and 'Floratam'. The plant material for a second experiment was derived from replicate mother pots that were refreshed with new potting medium between August $25^{th}$ and August $30^{th}$ in 2021 for each 'DALSA 1618' and four cultivars ('Amerishade®', 'DelMar', 'Floratam', and 'Raleigh'). Pots were fertilized every two weeks with 20-20-20 water soluble fertilizer and left untrimmed for 70 days. Data was collected on Nov. 8, 2021. For all sets of material, twelve samples were measured for each of seven traits using a digital caliper. Leaf length and leaf blade width were recorded from the first fully expanded leaf emerging from the $5^{th}$ node. Internode length and diameter were measured between the $5^{th}$ and $6^{th}$ nodes. Node diameter was measured horizontally on the $5^{th}$ node. The number of nodes within 30.5 cm were recorded for each stolon measured. Unmown leaf length was measured from the longest fully expanded leaves. Results showed that the leaf length of the first fully expanded leaf at the 5th node for 'DALSA 1618' (37.2 mm) is like 'Raleigh' and 'DelMar' and shorter than 'Amerishade®' and 'Floratam' (Table 1). Leaf width for 'DALSA 1618' (7.8 mm) is like 'DelMar' and 'Floratam' and wider than 'Amerishade®' and 'Raleigh'. The internode length for 'DALSA 1618' (85.4 mm) is like 'Raleigh' which was is shorter than 'Floratam' but longer than both 'Amerishade®' and 'DelMar'. The internode diameter of 'DALSA 1618' (2.8 mm) in this set of material is thicker than all four cultivars, while the node diameter is like 'Floratam' and 'Raleigh' which is wider than 'Amerishade®' and 'DelMar'. The average number of nodes within 30.5 cm for 'DALSA 1618' (4.0) was like 'Amerishade®' and 'Raleigh', but greater than 'Floratam', and less than 'DelMar'. The unmown leaf length of 'DALSA 1618' (21.5 cm) and 'Floratam' are similar in length, which was greater than 'Amerishade®', 'DelMar', and 'Raleigh'.

Field performance traits: In the 2012 Specialty Crop Research Initiative Shared Spaced-Plant Nurseries (SCRI SSPN), 'DALSA 1618' ranked 22$^{nd}$ out of 165 entries across all seven locations (College Station, TX; Dallas, TX; Gainesville, FL; Griffin, GA; Tifton, GA; 'Raleigh', NC; and Stillwater, OK) in 2012-2013 under normal management conditions, and it ranked 3$^{rd}$ under drought stress conditions (data not provided). Therefore, it was advanced for further environmental testing in the 2016 NTEP and 2016 SCRI RFT.

Turfgrass quality, spring greenup, leaf texture, genetic color, shoot density, seasonal color, drought tolerance, and resistance to pests and pathogens were all rated on a 1 to 9 scale where 9=excellent performance following NTEP guidelines (Morris and Shearman, 1999). Other traits such as establishment and green cover were rated either visually or digitally as a percentage. In the 2012 SCRI space-plant nursery, turfgrass quality was rated under non-stress (normal) and drought stress conditions. Actual means across all locations and years were regressed against predicted means and ranks were assigned from greatest mean quality to least mean quality. During the 2016 NTEP, establishment was rated periodically during the first full year as a percentage of plot cover. Traits evaluated included turfgrass quality (monthly), spring greenup, winterkill, leaf texture, genetic color, shoot density (spring, summer, and fall), seasonal color (fall and winter), drought tolerance (wilting, dormancy, recovery), and resistance to large patch (*Rhizoctonia solani* Kühn) and gray leaf spot diseases. In the 2016 SCRI RFT, percent green cover and turfgrass quality were rated in each location. Spring greenup, fall color retention, and resistance to gray leaf spot were additionally rated in Dallas, TX. The salinity tolerance study evaluated changes in quality, green cover, and total biomass over seven weeks in comparison to the freshwater control groups. Final means for each trait were divided by the freshwater control groups means to calculate a percent index.

During the 2017 St. Augustine Shade Study, plot establishment was digitally captured as percent green cover using a light box every two weeks from Aug. 11, 2017 through Oct. 6, 2017 and Jun. 28, 2018 through Oct. 4, 2018. Images were processed (Richardson et al., 2001) and batch analyzed (Karcher and Richardson, 2005) with hue settings of 45 to 120 and saturation settings of 10 to 100. All visual traits were rated on a 1 to 9 scale where 9=excellent and 1=very poor with 6=minimum acceptable. Turfgrass quality, plot color, and shoot density were rated every two weeks beginning Aug. 16, 2017 through Oct. 12, 2017 and from Jun. 28, 2018 through Oct. 4, 2018. Turfgrass quality was additionally rated monthly in 2019 from May 15$^{th}$ through September 17$^{th}$. Fall color was rated on Nov. 15, 2019. Spring greenup was rated on May 16, 2018 and Apr. 23, 2019. Prevalence of gray leaf spot was rated on Jul. 26, 2018 and Oct. 4, 2018. Winter injury from 2017 to 2018 killed all plots of 'Floratam', but 'DALSA 1618' and other cultivars survived in all three replications. Therefore, data from 'Floratam' will not be presented after 2017. Leaf lengths were measured with a ruler (cm) every two weeks before mowing events beginning on Aug. 22, 2017 through Oct. 6, 2017 and Jun. 28, 2018 through Oct. 5, 2018. The two longest unmown leaves in each plot were measured from the leaf tip to the base of the leaf collar. Average lengths and days since the last mowing event were then used to calculate daily leaf elongation rates (DER, mm·d-1).

During the herbicide tolerance study, turfgrass quality (1-9), establishment data (0-100%) and phytotoxicity (0-100%) were visually rated at each location. Turfgrass quality was rated monthly, establishment data was rated every two weeks until 95% establishment was reached, and phytotoxicity was rated every week for the duration of the herbicide residual. Data for the 2021 sod tensile strength study was collected on July 27 at both locations. Data included sod tensile strength (STS), sod handling quality (data not shown), and volumetric water content (VWC). Prior to data collection, each site conducted a dry down study in order to have consistent moisture content in the plots for harvesting.

All analyses, including principal components analysis, were performed using JMP Pro 10 (SAS Inc., Cary, NC). Morphological data were analyzed using the least squared means method with genotype as fixed effects, and experiments 1 and 2 will be presented separately. For traits rated on a 1 to 9 scale, entry, date or year, and entry by date or by year were treated as fixed factors and replications as random factors. Data were combined for each entry if interactions were not significant. For establishment, turfgrass quality, spring greenup and percent green cover data, means were compared by date of collection and not combined across dates. If the analysis of variance and effect tests were significant, means were separated using Fisher's protected LSD at the 0.05 probability level.

Figure 9:
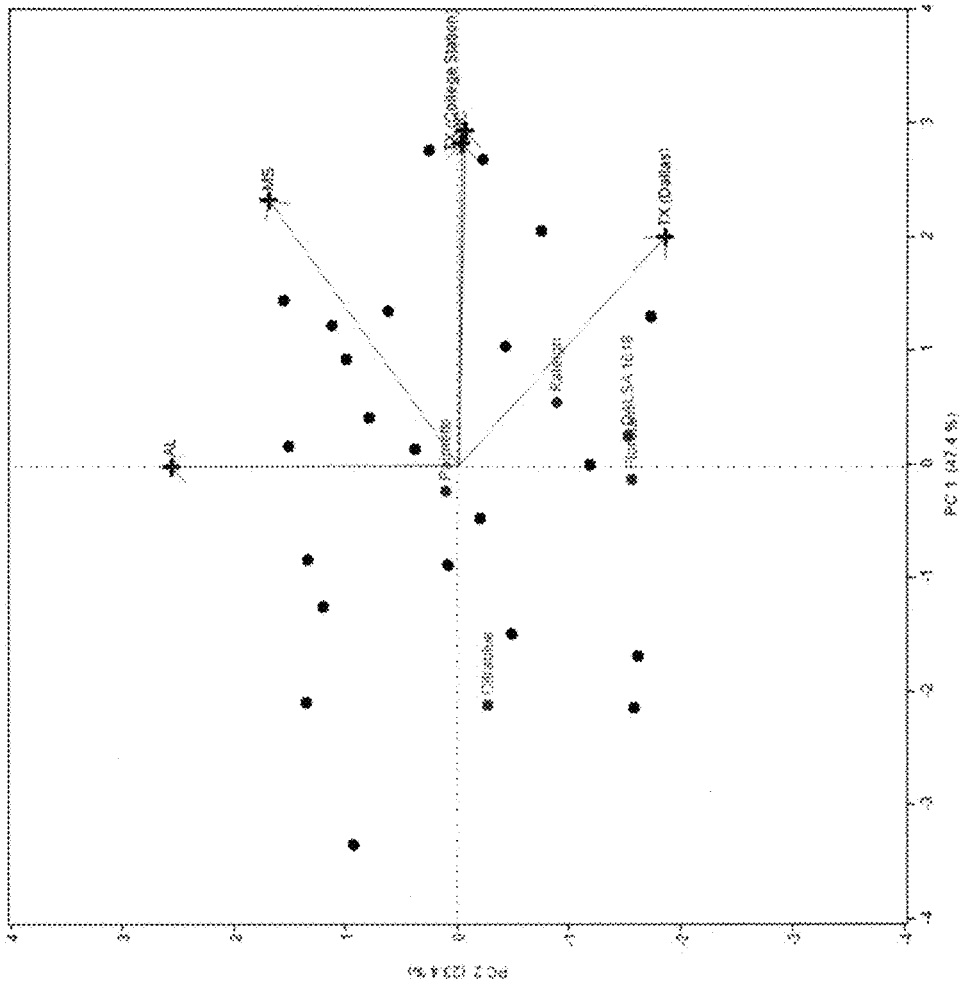
FIG. 9 Principal components analysis for mean percent establishment by the end of 2016 growing season in October (Auburn, AL and 'Raleigh', NC) and November (College Station, TX; Dallas, TX; and Starkeville, MS) during the 2016 National Turfgrass Evaluation Program (NTEP) for all 27 entries. Red arrows represent the locations and solid circles represent all 27 entries included in the 2016 NTEP. 'DALSA 1618' and commercial checks are displayed in blue, and rest of the other experimental entries are displayed in black.
Figure 10:
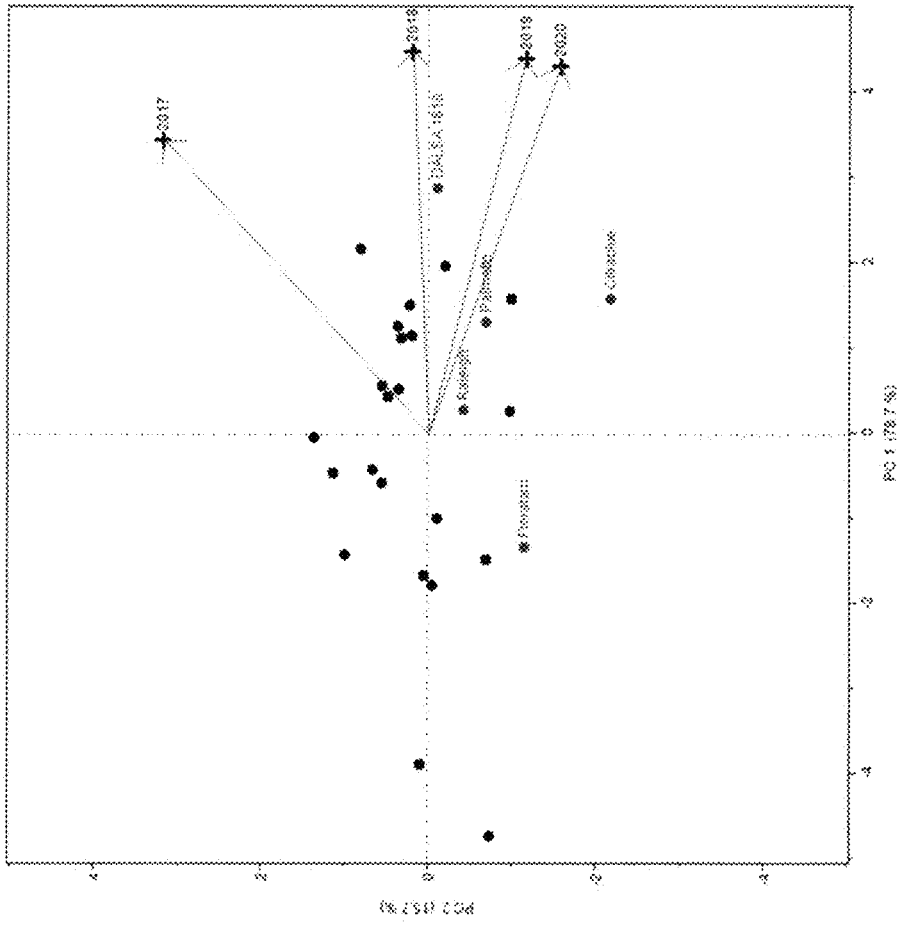
FIG. 10 Principal components analysis for mean turfgrass quality ratings for all 27 entries included in the 2016 NTEP. Data included mean turfgrass ratings across all ten locations (Citra, FL (chinch bug); Jay, FL; Ft. Lauderdale, FL (standard and low fertilizer); Griffin, GA; Dallas, TX; College Station, TX; Starkville, MS; Auburn, AL; and 'Raleigh', NC) in each year from 2017 to 2020. Red arrows represent the locations and solid circles represent all 27 entries included in the 2016 NTEP. 'DALSA 1618' and commercial checks are displayed in blue, and rest of the other experimental entries are displayed in black.
Figure 11:
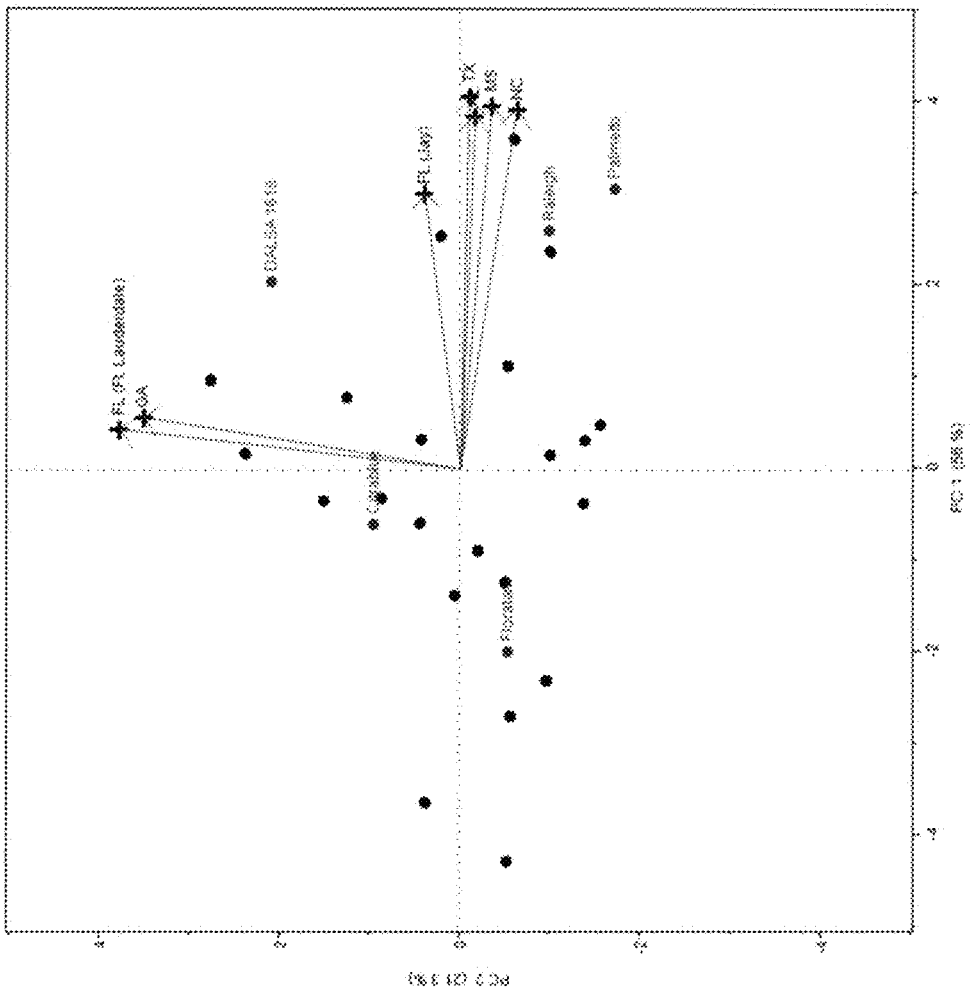
FIG. 11 Principal components analysis for mean spring greenup ratings for all 27 entries included in the 2016 NTEP. Data included mean spring greenup ratings from 2017 to 2020 in each of the seven locations (Jay, FL; Ft. Lauderdale, FL; Griffin, GA; Dallas, TX; Starkville, MS; Auburn, AL; and 'Raleigh', NC). Red arrows represent the locations and solid circles represent all 27 entries. 'DALSA 1618' and commercial checks are displayed in blue, and rest of the experimental entries are displayed in black.

Establishment: In the summer of 2016, each individual plot of the 2016 NTEP was planted with 18 square plugs measuring 8.3 cm in width. Plots were spaced 2.1 m apart. Establishment was rated as a percentage of plot coverage (0 to 100%). Five NTEP locations [TX (Dallas and College Station), MS (Starkville), AL (Auburn) and NC ('Raleigh')] reported mean percent establishment (Table 2). Three dates were selected in each location to demonstrate rate of establishment or plot coverage over time. In Dallas, TX, 'DALSA 1618' and 'Raleigh' had higher rates of establishment than other cultivars by September 2016, but 'DALSA 1618' was similar to all other cultivars by November 2016 reaching 80% establishment (Table 2). All cultivars reached nearly full establishment by June 2017. In College Station, TX, no differences were observed until November 2016 when 'DALSA 1618' reached nearly full establishment similarly to other cultivars except 'CitraBlue®' which was statistically slower. In Mississippi and Alabama, 'DALSA 1618' established similarly to other cultivars except for July 2016 in Alabama where 'DALSA 1618' had better establishment than 'Palmetto®' and 'Raleigh' but similar to 'CitraBlue®' and 'Floratam'. In North Carolina, 'DALSA 1618' established at a similar rate as other commercial cultivars in 2016. In May 2017, 'DALSA 1618', 'Floratam', and 'Palmetto®' had similar rates of establishment which were slower than 'Raleigh', but by August 2017, no statistical differences were observed between the four genotypes. 'DALSA 1618' was statistically faster than 'CitraBlue®' in 2017 (May and August) which may have experienced a loss of cover due to cold sensitivity. Principal components analysis (PCA) was conducted for 27 entries using the last establishment rating of the year in 2016 from each location (FIG. 9). Principal components 1 and 2 explained 47.4% and 23.4% of the variance, respectively. The PCA biplot did not show strong relationship between locations for establishment except 'Raleigh', NC and College Station, TX. In approximately 4 to 5 months after planting, some experimental lines (displayed in soild black circles) exhibited faster establishment rate as compared to 'DALSA 1618' and commercial cultivars. Overall, 'DALSA 1618' had similar establishment ratings as other tested cultivars which was superior than 'CitraBlue®' (Table 2).

Figure 3:
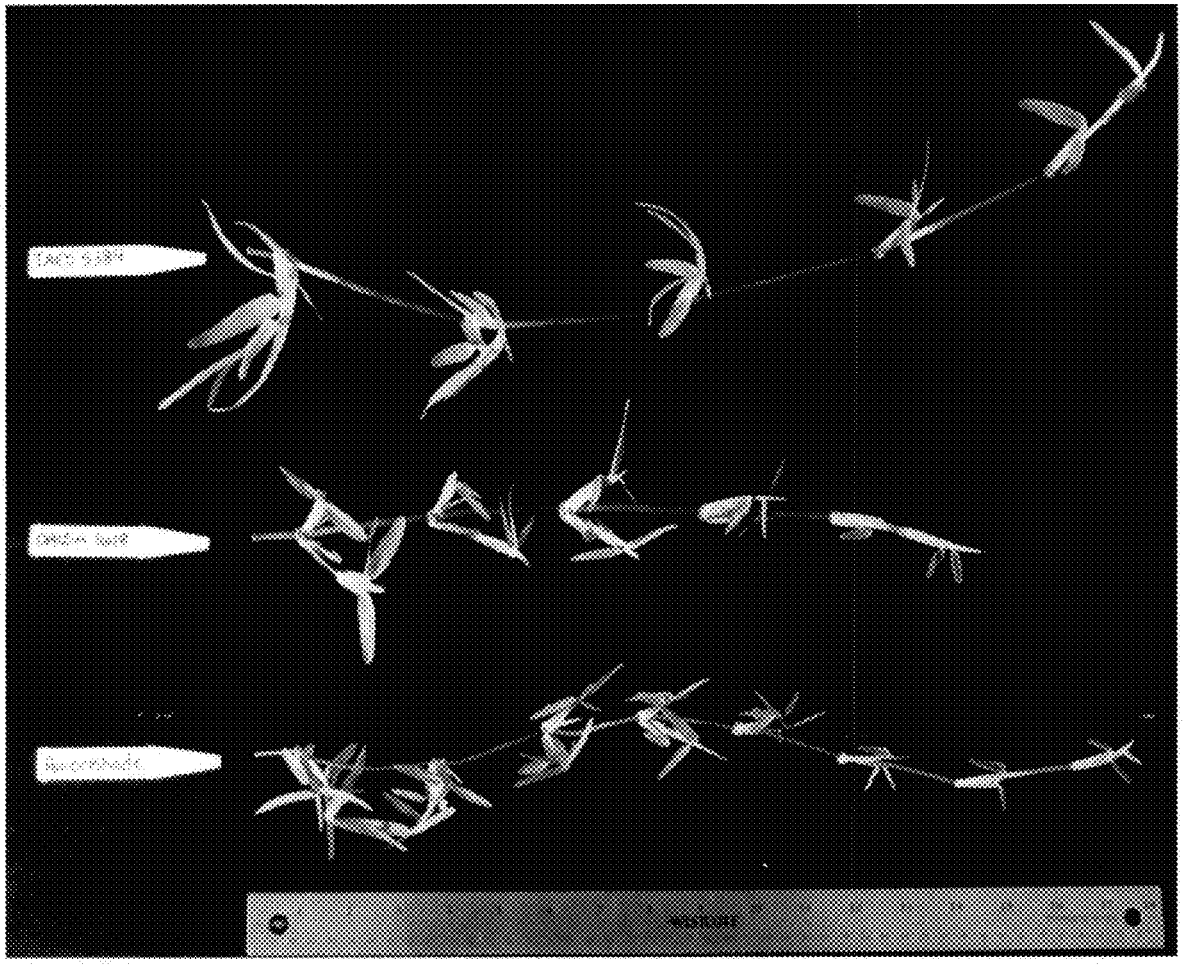
FIG. 3 Shows stolon characteristics of 'DALSA 1618' (middle stolon) compared to 'TAES 5384' (female parent; upper stolon) and 'Amerishade®' (male parent; bottom stolon). Photographed Mar. 16, 2022.

Turfgrass quality: Turfgrass quality is rated on a 1 to 9 scale where 1=brown or dead, 9=excellent and dark green, and 6=minimum acceptable. In the 2016 NTEP, turfgrass quality was reported by each of the trial locations from 2017 through 2020. The standard and ancillary trial locations were grouped for this report according to latitude or proximity to coastlines. Along latitudes 32 and 33 lies Dallas, TX (32.7767° N), Starkville, MS (33.4504° N), Auburn, AL (32.6099° N), and Griffin, GA (33.2468° N). Other locations such as 'Raleigh', NC, Jay, FL, Ft. Lauderdale, FL (standard and low fertilizer trials), Citra, FL (chinch bug trial), and College Station, TX (drought trial) were grouped as coastal and coastal ancillary locations. Across all latitude 32 and 33 locations, 'DALSA 1618' ranked in the top statistical group each year from 2017 through 2020 (Table 3). In Dallas, TX, 'DALSA 1618' exhibited superior turfgrass quality than 'Floratam' across all four years. The turfgrass quality of 'DALSA 1618' was similar to 'Raleigh' in all four years except in 2019 when 'DALSA 1618' exhibited superior quality. Likewise, the turfgrass quality of 'DALSA 1618' was similar to 'Palmetto®' in all years except 2017 when 'DALSA 1618' had better quality. 'DALSA 1618' had similar quality ratings as 'CitraBlue®' except in 2020 when the turfgrass quality of 'DALSA 1618' exceeded 'CitraBlue®'. In Mississippi, the quality of 'DALSA 1618' was similar to other cultivars except for in 2018 when 'DALSA 1618' had greater turfgrass quality than 'Floratam' (Table 3). In Alabama, the quality of 'DALSA 1618' was greater than other cultivars in 2017 and 2018. 'Floratam' and 'Raleigh' did not perform as well as other cultivars across all years. 'DALSA 1618' had similar quality to 'Palmetto®' in 2019, and similar quality as 'CitraBlue®' in 2020 which was better than other cultivars. No differences were observed between 'DALSA 1618' and other cultivars in Georgia. In the coldest trial location of North Carolina, the quality of 'DALSA 1618' was like 'Floratam' in 2017 but greater than 'Floratam' in 2018, 2019, and 2020 (Table 4). Compared to the cold tolerant cultivars, 'Palmetto®' and 'Raleigh', quality for 'DALSA 1618' was lower in 2017 but similar in other years. 'DALSA 1618' had higher quality than 'CitraBlue®' from 2017 to 2019, and similar quality in 2020. In Jay, FL, 'DALSA 1618' was like all cultivars in 2017 and 2019, but was better than 'Floratam' in 2018 and 'Raleigh' in 2020. In the standard trial in Ft. Lauderdale, FL 'DALSA 1618' was similar to 'Floratam', 'Palmetto®', and 'Raleigh', but had lower mean quality than 'CitraBlue®' from 2018 to 2020. Under a low fertilizer regime (Ft. Lauderdale, FL), 'DALSA 1618' retained higher turfgrass quality than 'Floratam', 'Palmetto®', and 'Raleigh' in 2018 (Table 5). In 2019, turfgrass quality for 'DALSA 1618' was similar to 'Floratam' and 'Raleigh' but less than 'Palmetto®'. In 2020, the quality was similar among the four cultivars. 'CitraBlue®' had the highest quality in all four years which was greater than 'DALSA 1618'. Under drought conditions (College Station, TX), 'DALSA 1618' was a top performer across four years with above acceptable quality of 6.0. Mean quality was similar among genotypes in 2017 and 2020. Compared to the drought tolerant cultivar, 'Floratam', 'DALSA 1618' had higher mean quality in 2018 and 2019. 'DALSA 1618' also had higher quality than 'Raleigh' in 2018 and 'CitraBlue®' in 2019. 'DALSA 1618' and 'Palmetto®' were similar across all years. During the chinch bug trial in Citra, FL, all genotypes had above acceptable quality in both 2017 and 2018, though 'DALSA 1618' had higher quality in both years than 'Floratam', the chinch bug resistant cultivar. Mean quality was similar between 'DALSA 1618' and 'CitraBlue®' both years. Although 'DALSA 1618', 'Palmetto®', and 'Raleigh' had similar quality in 2017, 'DALSA 1618' was higher in 2018. As an interploid hybrid, 'DALSA 1618' demonstrates high turfgrass quality across the southeastern United States as far west as Dallas, TX (USDA plant hardiness zone of 8a), as far north as 'Raleigh', NC (USDA plant hardiness zone of 7b), and as far south as Ft. Lauderdale, FL (USDA plant hardiness zone of 10b). Principal components analysis was conducted using mean turfgrass quality of 27 entries across all locations for each of the four years (FIG. 3). Principal component 1 and 2 explained 78.7% and 15.7% of the variance, respectively. The PCA biplot showed higher correlation between turfgrass quality ratings from 2018, 2019 and 2020, where 'DALSA 1618' was one of best performing genotypes (better than 'Raleigh' and 'Palmetto®') and 'Floratam' was a poor performing genotype.

Figure 4:
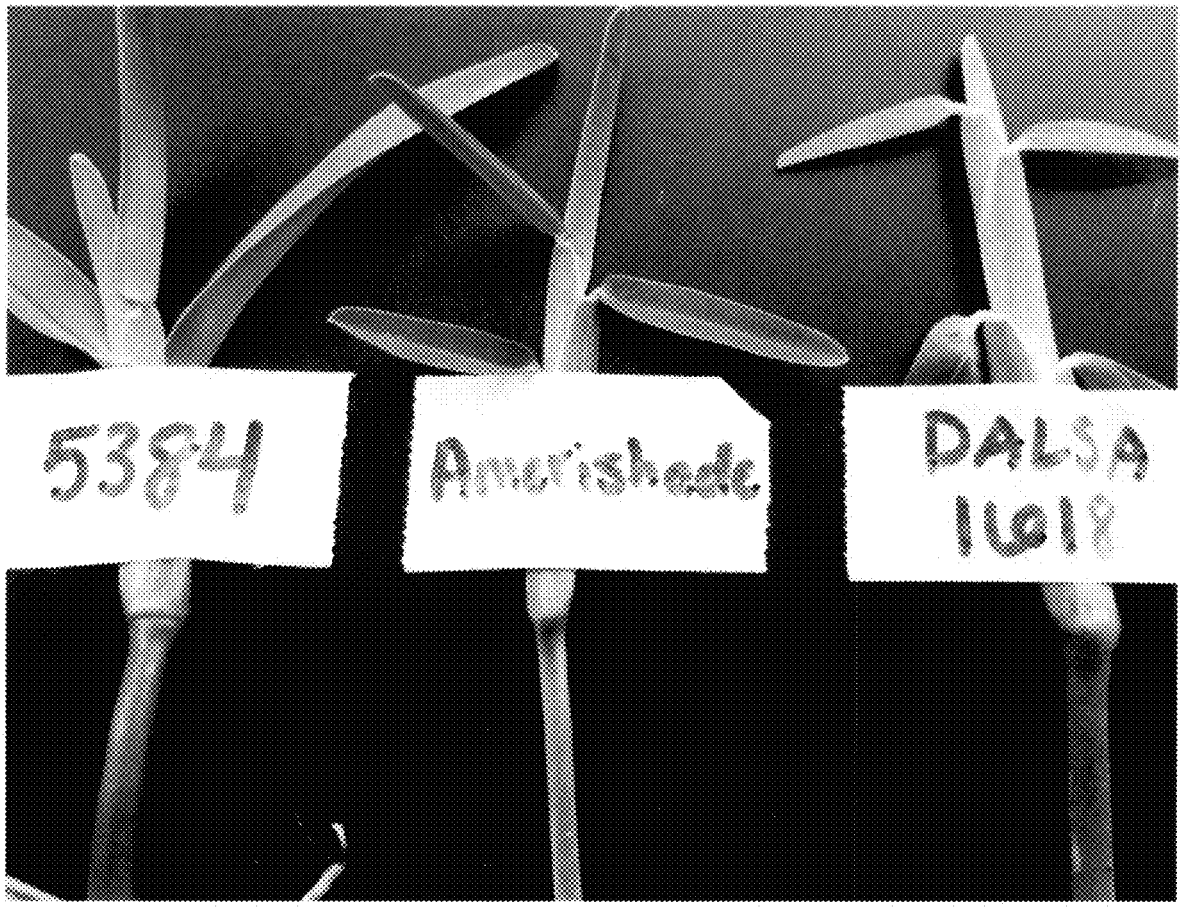
FIG. 4 Shows node and internode coloring of 'DALSA 1618' (far right) compared to 'TAES 5384' (female parent) and 'Amerishade®' (male parent).
Figure 5:
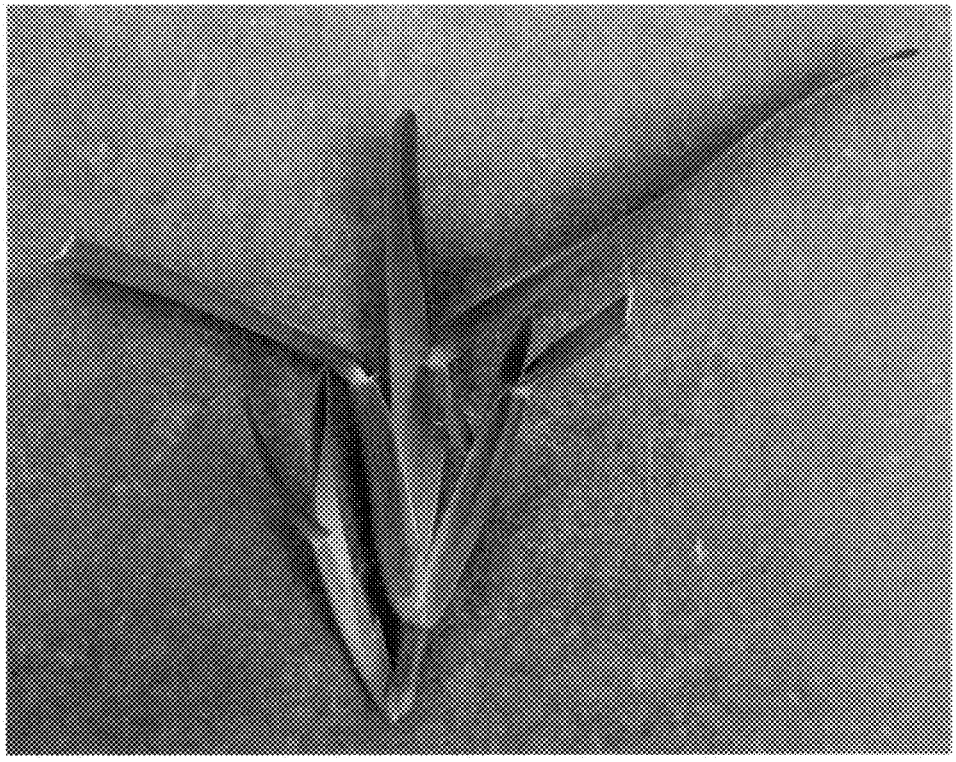
FIG. 5 Shows vegetative growth of new leaf tissue of 'DALSA 1618'. New leaves are dark green and when expanded, keel towards the base of the leaf.
Figure 6:
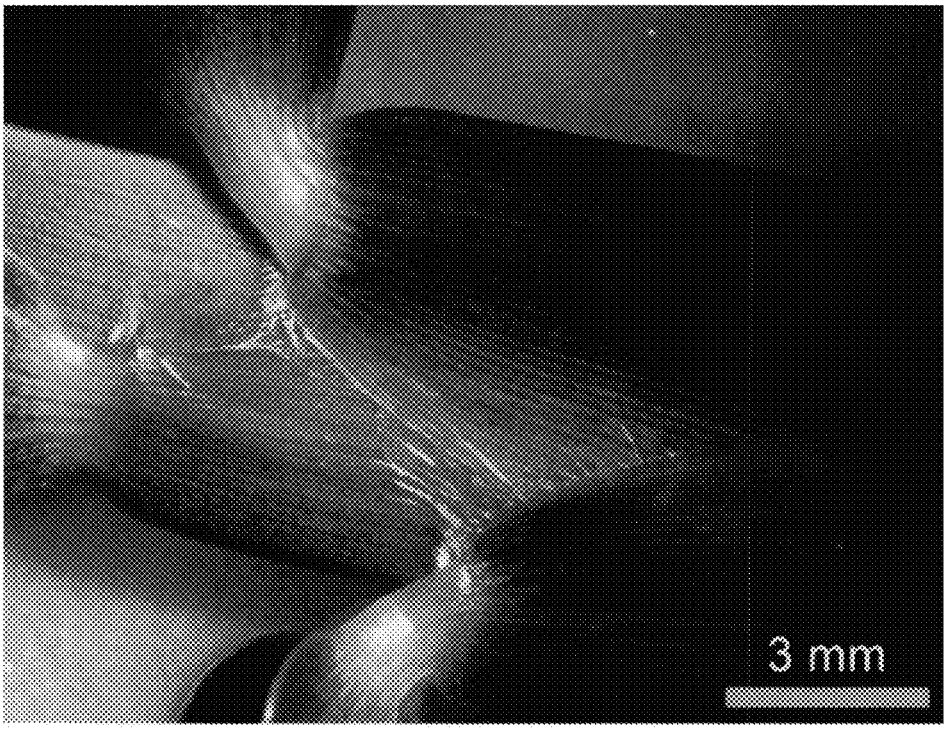
FIG. 6 Shows leaf sheath hairs at the collar of 'DALSA 1618'.

Spring greenup: Spring greenup was rated from 2017 to 2020 in the 2016 NTEP across 10 locations, seven of which are standard locations (Dallas, TX; Starkville, MS; Auburn, AL; Griffin, GA; 'Raleigh', NC; Jay, FL; and Ft. Lauderdale, FL) and three are ancillary locations (Ft. Lauderdale, FL—low fertilizer; College Station, TX—drought; and Citra, FL—chinch bug). The spring greenup of 'DALSA 1618' was fairly consistent across latitudes 32 and 33 where it was greater than or equal to 'CitraBlue®', and less than or equal to 'Palmetto®' and 'Raleigh' (cold tolerant cultivars) (Table 6). Compared to 'Floratam', spring greenup was higher for 'DALSA 1618' except in AL in 2020 and GA where they were similar. In summary, 'DALSA 1618' emerges from winter along latitudes 32 and 33 with spring greenup that is better than the cold sensitive polyploid cultivar, 'Floratam', but is less than or equal to the cold tolerant diploid cultivars 'Palmetto®' and 'Raleigh'. In the northernmost location of 'Raleigh', NC, 'DALSA 1618' had mean greenup less than or equal to the cold tolerant cultivars, 'Raleigh' and 'Palmetto®', which was greater than 'Floratam' and greater than or equal to 'CitraBlue®' (Table 7). In Jay, FL, greenup was similar between 'DALSA 1618' and 'CitraBlue®' which was greater than or equal to 'Floratam', 'Palmetto®', and 'Raleigh'. 'DALSA 1618' was a top performer in Jay, FL in terms of greenup from 2018 to 2020. Performance was similar to that of Jay, FL in Ft. Lauderdale, FL where 'DALSA 1618' has superior greenup as did 'CitraBlue®' and better greenup than 'Floratam', 'Palmetto®', and 'Raleigh' under standard conditions. In these three standard coastal locations, 'DALSA 1618' exhibited superior spring greenup similar to 'CitraBlue®' which was most often better than other cultivars. Under low fertilizer trial management in Ft. Lauderdale, FL, 'DALSA 1618' and 'CitraBlue®' had superior greenup to other cultivars comparable to its performance under standard trial conditions (Table 8). Following recovery from drought trials in College Station, TX, 'Palmetto®' and 'Raleigh' had high greenup in each of four years. Comparatively, spring greenup for 'DALSA 1618' was less than or equal to both cultivars, but also similar to 'CitraBlue®', and earlier than or similar to 'Floratam'. Neither of the five genotypes were top performers in Citra, FL in 2017, but all had similar spring greenup. In 2018, 'DALSA 1618' and 'CitraBlue®' had superior greenup to 'Floratam', 'Palmetto®', and 'Raleigh'. In these three ancillary locations, 'DALSA 1618' and 'CitraBlue®' were similar for greenup, and compared to 'Floratam', greenup for 'DALSA 1618' was either better or similar. Principal components analysis was conducted using mean spring greenup ratings of 27 entries across all years (2017 to 2020) for each of the seven standard locations (FIG. 4). Principal component 1 and 2 explained 56.0% and 21.3% of the variance, respectively. The PCA biplot showed higher correlation between five locations ('Raleigh', NC; Starkville, MS; Auburn, AL; Dallas, TX; and Jay, FL). 'Raleigh' and 'Palmetto®' were best performing cultivars in these environments. Mean spring greenup in Griffin, GA and Ft. Lauderdale, FL were highly correlated. Overall, based on its placement in the PCA biplot, 'DALSA 1618' was one of better performing genotypes for spring greenup across all locations and exhibited better spring greenup than 'Floratam' and 'CitraBlue®'.

Winter survival: Damage from cold and freezing temperatures can be rated following spring greenup as a percentage of total plot area or on a 1 to 9 scale where 1=complete loss and 9=no damage evident. Compared to cold-tolerant 'Palmetto®' and 'Raleigh', 'Floratam' is cold-sensitive and generally had lower percent living cover and higher winterkill across all presented locations (Table 9). 'DALSA 1618' had better winter survival than 'Floratam' in Starkville, MS and better or similar survival in other locations. Percent living cover and winterkill for 'DALSA 1618' was less than or equal to 'Palmetto®' and 'Raleigh', particularly in the coldest location of 'Raleigh', NC. 'DALSA 1618' had winter survival greater than or equal to 'CitraBlue®'. No differences were observed between 'DALSA 1618' and tested cultivars for plot loss in Ft. Lauderdale, FL under standard or low fertilizer trial management (data not shown).

Genetic color: Genetic color is rated on a 1 to 9 scale where 1=brown or dormant and 9=dark green. Six standard and two ancillary NTEP locations rated genetic color. Under non-stress conditions of the standard trials, 'DALSA 1618' is darker green than 'Raleigh' and lighter green than 'CitraBlue®', and similar to 'Floratam' and 'Palmetto®' (Table 10). Under a low fertilizer regime (Ft. Lauderdale, FL), 'DALSA 1618' had similar genetic color as 'Floratam', 'Palmetto®' and 'Raleigh' but was lighter green as compared to 'CitraBlue®'. Under drought stress conditions (College Station, TX), 'DALSA 1618' and 'Floratam' (drought resistant standard) retained a darker green color than 'CitraBlue®', 'Palmetto®', and 'Raleigh'.

Shoot density: Shoot density is rated seasonally in spring, summer, and fall on a 1 to 9 scale where 1=very sparse or thin and 9=very dense. Two standard NTEP locations (Jay, FL and Ft. Lauderdale, FL) reported shoot density for all three seasons, and Dallas, TX only reported summer density. The mean shoot density of 'DALSA 1618' in the spring season was similar to 'CitraBlue®', 'Palmetto®', and 'Raleigh', but denser than 'Floratam' which is a cold sensitive cultivar (Table 10). In the summer season, the shoot density of 'DALSA 1618' was similar to 'CitraBlue®' and higher than 'Floratam', 'Palmetto®' and 'Raleigh' which is indicative of its superior summer performance. In the fall season, 'CitraBlue®' had the highest shoot density, but no difference was observed between 'DALSA 1618' and other tested cultivars. Shoot density was additionally reported for all three seasons under low fertilizer management (Ft. Lauderdale, FL). In the spring, the shoot density of 'DALSA 1618' is less than 'CitraBlue®' but similar to other tested cultivars. In the summer, 'DALSA 1618' is dense like 'CitraBlue®', 'Floratam', and 'Palmetto®' but denser than 'Raleigh'. In the fall, shoot density for 'DALSA 1618' is less than 'CitraBlue®', similar to 'Floratam' and 'Palmetto®', and denser than 'Raleigh'. Under standard and low fertilizer regimes, 'DALSA 1618' retains a high shoot density.

Seasonal color: Fall and winter color retention were rated on a 1 to 9 scale where 1=completely dormant and 9=completely green. In September, 'CitraBlue®' retained higher fall color than 'DALSA 1618' and other cultivars, but no differences were evident in October (Table 11). In November, 'CitraBlue®' again had the highest fall color retention compared to the other four genotypes, but 'DALSA 1618' was similar to 'Floratam' and 'Palmetto®' and higher than 'Raleigh'. Winter color retention for 'DALSA 1618' was like that of 'Palmetto®' and 'Raleigh' in Dallas, TX and Jay, FL which was betterthan 'CitraBlue®' and 'Floratam'. Under the standard trial conditions in Fort Lauderdale, FL, 'DALSA 1618' is similar to the tested cultivars, but under low fertilizer conditions 'DALSA 1618' did not retain its color as well as 'CitraBlue®' though it was similar to 'Floratam', 'Palmetto®', and 'Raleigh'. Winter color retention in College Station, TX was similar between 'DALSA 1618' and cultivars. In Citra, FL, 'DALSA 1618', 'CitraBlue®', 'Palmetto®', and 'Raleigh' all held their color better than 'Floratam'. Overall, 'DALSA 1618' retains its seasonal color similarly to 'Palmetto®' and 'Raleigh' which is better than 'Floratam'.

Seedhead density: Seedhead density is rated in the summer months on a 1 to 9 scale where 1=very heavy and 9=no seedheads present. Presence of seedheads is detrimental to turfgrass quality and therefore, presence of fewer seedheads is a desirable characteristic. In Starkville, MS, 'DALSA 1618' seedhead density (5.0) was lower than 'Raleigh' (3.7) but similar to 'Palmetto®' (4.0) and greater than 'CitraBlue®' (8.3) and 'Floratam' (7.7) (table not shown). In 'Raleigh', NC, 'DALSA 1618' (7.3) produced fewer seedheads than 'CitraBlue®' (3.0) and similar seedheads to other cultivars. Mean seedhead production with weekly mowing in Dallas, TX was scored based on one rating in 2017 and two in each 2018 and 2019. 'DALSA 1618' (6.1) produced fewer seedheads than 'Palmetto®' (5.1) and 'Raleigh' (5.3) but more than 'Floratam' (7.1) and 'CitraBlue®' (7.6).

Disease resistance: Large patch and gray leaf spot are two problematic diseases encountered with St. Augustinegrass. Resistance to disease is rated on a 1 to 9 scale where 1=completely diseased and 9=no disease evident. In the final 2016 NTEP report, evidence of large patch disease was rated in only a few standard locations (Dallas, TX; Starkville, MS; and 'Raleigh', NC) where ratings were very high indicating very little disease present and no statistical differences between 'DALSA 1618' and other cultivars (Table 12). Large patch was additionally rated in Citra, FL where 'DALSA 1618' showed greater resistance than 'Palmetto®' and was like other cultivars. Gray leaf spot prevalence was observed with more prevalence. In Dallas, TX, no differences were observed between 'DALSA 1618' and cultivars in the 2016 NTEP. 'DALSA 1618' and 'CitraBlue®' had superior resistance compared to 'Floratam', 'Palmetto®', and 'Raleigh' in Starkville, MS and 'Raleigh', NC. No differences were observed in Ft. Lauderdale, FL among all genotypes tested in the standard trial, but 'DALSA 1618' was equally susceptible as 'Floratam', 'Palmetto®', and 'Raleigh' under low fertilizer management. In the chinch bug study in Citra, FL, 'DALSA 1618' and 'Raleigh' showed no evidence of disease which were like 'Palmetto®' and 'CitraBlue®' while 'Floratam' was very susceptible. More testing is neeed to fully evaluate large patch resistance of 'DALSA 1618', but its level of resistance to gray leaf spot is comparable to other cultivars depending on trial conditions.

Figure 12:
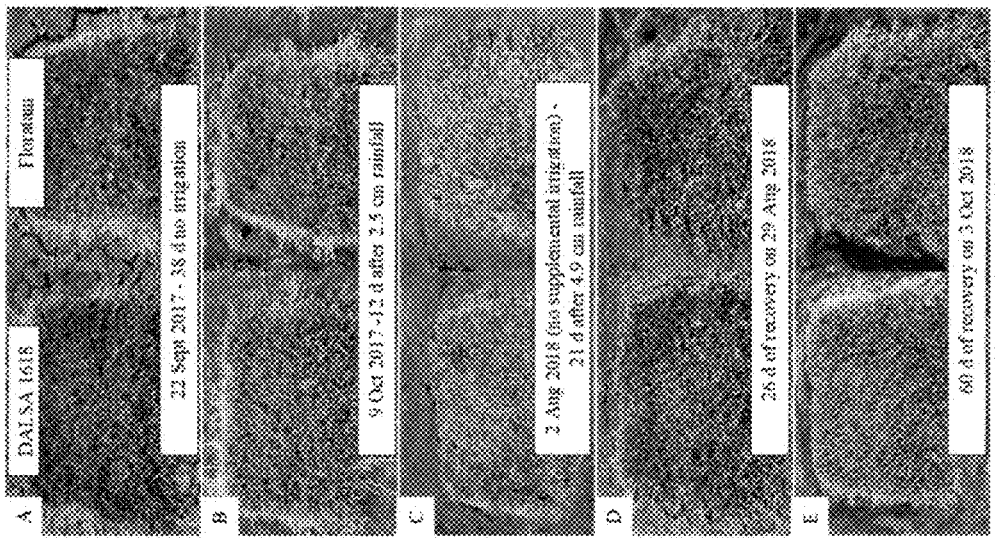
FIG. 12 Shows drought stress and recovery of 'DALSA 1618' and 'Floratam' during the 2016 Specialty Crop Research Initiative Replicate Field Trial (SCRI RFT) in Dallas, TX. Irrigation to initiate recovery supplements rainfall at 2.5 cm per week.

Drought resistance: Drought resistance during the 2016 NTEP trial was evaluated in College Station, TX in three parts as wilting (before severe stress), dormancy (after severe stress), and recovery (upon initiating irrigation or heavy rainfall). All three traits were rated on a 1 to 9 scale where 1=complete wilting, dormancy, or dead plant and 9=no wilting or dormancy and complete recovery. 'DALSA 1618' was more resistant to wilt than 'Floratam', 'Palmetto®', and 'Raleigh' across four years and performed similarly to 'CitraBlue®' (Table 13). During severe stress, 'DALSA 1618' was more resistant to drought-induced dormancy as compared 'Palmetto®' and 'Raleigh' but was similar to 'CitraBlue®' and 'Floratam', the most drought tolerant cultivar. All tested genotypes except 'Raleigh' recovered well from the drought stress. As part of the 2016 SCRI RFT, the percent green cover retention of 'DALSA 1618' was tested in College Station, TX under varying water conservation methods (approaches A and B) in 2017 and 2018. Under approach "A", 'DALSA 1618' retained green cover similarly to 'Floratam' (standard for drought resistance) under all irrigation levels except for once weekly treatments on 26 Apr. 2017 and 1 Jun. 2018, the first data point in each year (Table 14). At these times, percent green cover for 'DALSA 1618' was higher than 'Floratam'. Results from approach "B" were generally similar to approach "A" where percent green cover retention was like 'Floratam' but also 'Palmetto®' for all dates evaluated (Table 15). Turfgrass quality was additionally evaluated under drought stress for approaches A, B, and C (Dallas, TX) on a 1 to 9 scale where 6=minimum acceptable. For approach "A", no differences were observed between 'DALSA 1618' and 'Floratam' within each treatment in 2017 where both genotypes had quality ratings above the minimum acceptable level (Table 14). In 2018, mean quality for both genotypes were below acceptable when irrigated less than once every two weeks. However, 'DALSA 1618' has a higher quality than 'Floratam' for reduced irrigation at once every two weeks and once weekly. No differences were observed when irrigation was applied twice weekly. These results are slightly different from Erikson et al. (2019) who performed a similar study in Florida which included other elite experimental lines, 'CitraBlue®', 'Palmetto®', and 'TamStar®' (also known as 'Dalsa 0605'; U.S. Plant Pat. No. 27,393). Over the course of their 20-month study, 'DALSA 1618' had superior quality to all three commercial cultivars in all irrigation treatments including the most restrictive bimonthly, monthly, and unirrigated regimes. Perhaps the inclusion of more genotypes in this study and geographical location imparted better separation between 'DALSA 1618' and 'Floratam'. Under approach "B", no differences in quality were observed between 'DALSA 1618', 'Floratam', and 'Palmetto®' in 2017 when irrigation was only applied once per week (Table 15). A reduction in irrigation to once every two weeks in 2018 reduced quality ratings for all entries, but 'DALSA 1618' and 'Floratam' maintained a greater quality than 'Palmetto®' suggesting improved drought resistance. The protocol for approach "C" was to refrain from applying supplemental irrigation after plots were fully established. A brief drydown period was conducted from 15 August to 27 Sep. 2017, and no irrigation was applied in 2018 or 2019. Recovery was initiated following each drought period through supplemental irrigation at summers end. Normal quality was rated in the spring and early summer when rain was prevalent and temperatures were cooler. In 2016, quality means were similar when irrigation was applied regularly to promote establishment. However, when supplemental irrigation was suspended in each of the following three years, 'DALSA 1618' had higher quality early in the season and during drought and recovery (late season) compared to 'Floratam', 'Palmetto®', and 'Raleigh' (Table 16). According to Chang et al. (2021), 'DALSA 1618' maintained turfgrass quality and delayed wilting and leaf firing into the later stages of drought which the authors theorize may have been through deeper rooting or stomatal regulation. When irrigation was resumed, 'DALSA 1618' recovered quicker from drought-induced dormancy compared to 'Floratam', 'Palmetto®' and 'Raleigh' which was reflected with a higher mean quality from greater shoot density. These differences between 'DALSA 1618' and 'Floratam' were captured during drought and recovery in 2017 and 2018 (FIG. 12). Following summers where no supplemental irrigation was applied, the fall color retention, spring greenup, and resistance to gray leaf spot for 'DALSA 1618' was superior to 'Floratam', 'Palmetto®', and 'Raleigh' (Table 16).

Shade avoidance: In 2017, 'DALSA 1618' and three shade tolerant diploids, 'Amerishade®', 'Palmetto®', and 'Raleigh', and one shade intolerant polyploid, 'Floratam', were planted under moderate shade density (63%) in Dallas, TX. Percent establishment was periodically captured and analyzed from digital images beginning at 22 d after planting in 2017 and ending at 428 d after planting in 2018. In 2017, no differences were observed between 'DALSA 1618' and the tested cultivars (Table 17). In 2018, 'DALSA 1618' also had similar establishment to the shade tolerant diploid cultivars, but was much greater than the shade intolerant cultivar, 'Floratam' which did not recover from the 2017-2018 winter. Additionally, 'DALSA 1618' retained high turfgrass quality which over time exceeded that of the 'Amerishade®', 'Palmetto®', and 'Raleigh'. The plot color and shoot density of 'DALSA 1618' under shade is similar to 'Amerishade®' which is darker green and denser than 'Palmetto®' and 'Raleigh' (Table 18). Fall color retention, spring greenup, and gray leaf spot resistance were similar between genotypes. Etiolation or elongation of leaf and stems is a typical shade avoidance response in warm season turfgrasses. One method to study and compare this physiological response between genotypes is to measure the daily elongation rate (DER, mm·d-1) of the leaves under shaded environment. Genotypes that exhibit reduced DER under shade tend to be better adapted to low-light conditions. The DER for 'Amerishade®', the semi-dwarf shade tolerant cultivar, was lower than all other tested genotypes in 2017 and 2018 (Table 18). 'DALSA 1618' has a DER like diploids, 'Palmetto®' and 'Raleigh', both of which have reasonably good shade tolerance. Surprisingly, the DER for 'DALSA 1618', 'Palmetto®', and 'Raleigh' were also like 'Floratam', the shade sensitive cultivar in this study, that did not survive the combined effects of cold and shade stress going into 2018. The results suggest that 'DALSA 1618' has good shade tolerance under moderate shade levels which is a marked improvement as a polyploid compared to 'Floratam'.

Salinity tolerance: Tolerance to saline irrigation water is important in areas where freshwater resources are restricted for outdoor irrigation and consumers may consider using reclaimed water for landscape irrigation. Chavarria et al. (2019) showed that compared to other major warm season turfgrass species, St. Augustinegrass is considerably intolerant to salinity stress though all species show a decline in quality as salinity levels increase. However, among St. Augustinegrasses the cultivar 'Seville' is twice as salt tolerant as 'Floratam' at levels <10 dS·m-1 (Dudeck et al., 1993). Under controlled environmental conditions, no statistical differences were observed among 'DALSA 1618', 'Floratam', 'Palmetto®', 'Raleigh', and 'Seville' when irrigated with freshwater (data not shown). At 15 dS·m-1 salinity concentration, 'DALSA 1618', 'Palmetto®', and 'Seville', had mean quality ratings ≥90% of the control group, which was greater than 'Floratam' and 'Raleigh' at 80% (data not shown). Final quality was lower at 30 dS·m-1 and very low at 45 dS·m-1, and differences were not significant among cultivars. Other visual differences for final green cover and total biomass were also not significant at any concentration level. These results indicate that further testing may be required and that although green cover and biomass were similar among genotypes, at 15 dS·m-1 'DALSA 1618' retains its quality similarly to the most salt tolerant St. Augustinegrass, 'Seville', which is greater than the salt-sensitive cultivar, 'Floratam'.

Herbicide tolerance: Herbicide tolerance is an important characteristic for production and management of St. Augustinegrass. In 2019 and 2020, College Station and Dallas research sites showed no visible phytotoxicity on 'DALSA 1618' from commonly used pre-emergence (oxadiazon G, pendimethalin, atrazine, and metolachlor) and post-emergence (2,4-D, dicamba, mecoprop) herbicides (data not shown). 'DALSA 1618' also exhibited a faster rate of establishment than 'Floratam' and 'Raleigh' in this study at six, 10 and 36 weeks after planting. On an average, 'DALSA 1618' (56.84%), established faster than 'Raleigh' (41.1%) and 'Floratam' (43.0%) in College Station and Dallas when planted using plugs 30.5 cm apart (Table 19).

Sod harvestability: Sod harvestability and blockability are important charaterisitcs for any vegetatively propagated cultivar to be successful in the marketplace and commercialy viable. Soil moisture content that is either too high or too low negatively compromises sod harvestablity and strength. The VWC on average at each location was 24.2% and 18.5% in College Station and Dallas, respectively. 'DALSA 1618' showed higher STS than 'Raleigh' and 'Floratam' in College Station, but was not significantly different than these two commercial cultivars in Dallas (Table 20). Variable soil type (sandy loam in College Station vs clay in Dallas), VWC, and environmental differences between locations could help explain observed STS differences between locations. Nonetheless, 'DALSA 1618' exhibited superior or acceptable STS in Dallas and College Station when compared to commercially available standards.

In summary, 'DALSA 1618' is an interploid hybrid St. Augustinegrass that when compared to the polyploid, 'Floratam', has a similar leaf blade width and stolon thickness, but shorter leaf length and stolon internode length. The performance of 'DALSA 1618' varied depending on the geographic locations and environmental conditions. Overall, 'DALSA 1618' established faster than 'CitraBlue®' and similarly to other tested commercial cultivars. Along latitudes 32 and 33 and coastal locations, 'DALSA 1618' exhibited high turfgrass quality which was generally higher than 'Floratam'. In Ft. Lauderdale, FL, the quality ratings of 'DALSA 1618' was not as high as 'CitraBlue®' but maintained acceptable quality similar to other cultivars. When drought stressed, 'DALSA 1618' retains a darker green color and higher quality longer like the most drought tolerant cultivar, 'Floratam', such that it can tolerate reduced irrigation rate of once every two weeks when weekly irrigation is not available or restricted. Under the combined stressor of cold and shade, 'DALSA 1618' performed better than 'Floratam' which is both cold and shade sensitive. Under moderate shade, 'DALSA 1618' maintains its genetic color and high shoot density like shade tolerant diploid cultivars which contributes to its high turfgrass quality. The leaf elongation rate of 'DALSA 1618' is also like that of shade tolerant diploids 'Palmetto®' and 'Raleigh'. As an interploid hybrid, 'DALSA 1618' exhibited early greenup which was better than 'Floratam' and in most environments was like 'Raleigh'. Furthermore, 'DALSA 1618' expresses less cold sensitivity than 'Floratam' and 'CitraBlue®'. In summary, 'DALSA 1618' exhibits comparable establishment and drought resistance to 'Floratam' but with improved turfgrass quality, spring greenup, and cold and shade tolerances. 'DALSA 1618' has the same level of tolerance to large patch as other cultivars, but requires further testing. As for gray leaf spot, 'DALSA 1618' is like that of 'CitraBlue®' and either comparable to or better when compared to other tested cultivars. These combinations of traits are unique in a St.

Augustinegrass cultivar, which should allow 'DALSA 1618' to succeed in multiple environments across the southern United States.

TABLE 1

Leaf blade and stolon characteristics of 'DALSA 1618' compared to commercial cultivars on Mar. 13, 2020 (Experiment 1) and Nov. 8, 2021 (Experiment 2) after 43 and 70 days untrimmed, respectively.

| | Cultivar | Leaf Length† | Leaf Width† | Internode Length‡ | Internode Diameter‡ |
|---|---|---|---|---|---|
| | | | mm | | |
| Experiment 1 | 'DALSA 1618' | 42.7 b | 6.0 a | 66.8 c | 3.0 a |
| | 'Captiva ®' | 24.8 d | 4.6 b | 43.7 f | 2.0 d |
| | 'Floratam' | 61.0 a | 5.9 a | 89.3 a | 2.9 a |
| | 'Palmetto ®' | 34.9 c | 5.0 b | 60.6 d | 2.3 c |
| | 'Raleigh' | 39.1 bc | 4.8 b | 74.1 b | 2.4 bc |
| | 'Seville' | 28.1 d | 4.6 b | 53.2 e | 2.6 b |
| | LSD†† | 5.8 | 0.6 | 5.2 | 0.2 |
| Experiment 2 | 'DALSA 1618' | 37.2 c | 7.8 a | 85.4 b | 2.8 a |
| | 'Ameri-shade ®' | 51.6 b | 5.0 c | 65.0 c | 1.7 d |
| | 'DelMar' | 39.3 c | 7.3 ab | 60.5 c | 2.1 c |
| | 'Floratam' | 65.7 a | 8.3 a | 99.0 a | 2.5 b |
| | 'Raleigh' | 48.3 bc | 6.3 b | 80.8 b | 2.0 c |
| | LSD†† | 11.7 | 1.2 | 9.0 | 0.2 |

| | | Node Diameter§ | Nodes within 12"¶ | Unmown Leaf Length# |
|---|---|---|---|---|
| | | mm | | cm |
| Experiment 1 | 'DALSA 1618' | 10.1 a | 5.0 b | 9.5 c |
| | 'Captiva ®' | 6.7 c | 6.1 a | 9.8 bc |
| | 'Floratam' | 10.2 a | 3.7 d | 18.1 a |
| | 'Palmetto ®' | 8.2 b | 4.6 bc | 10.5 bc |
| | 'Raleigh' | 8.2 b | 4.1 cd | 9.8 c |
| | 'Seville' | 8.3 b | 6.0 a | 11.1 b |
| | LSD†† | 0.9 | 0.5 | 1.3 |
| Experiment 2 | 'DALSA 1618' | 8.1 a | 4.0 b | 21.5 a |
| | 'Ameri-shade ®' | 5.7 c | 4.3 b | 16.7 b |
| | 'DelMar' | 6.9 b | 4.7 a | 16.7 b |
| | 'Floratam' | 8.3 a | 3.3 c | 23.2 a |
| | 'Raleigh' | 7.5 ab | 3.9 b | 18.3 b |
| | LSD†† | 0.8 | 0.4 | 2.6 |

†Leaf blade length and width were measured from the first fully expanded leaf blade of the 5th node.
‡Internode length and diameter were measured between the 5th and 6th nodes.
§Node diameter was measured horizontally on the 5th node.
¶The number of nodes within 12 inches was visually recorded compared to a ruler.
#Unmown leaf length was measured from the longest fully expanded leaves.
††All data are means from twelve stolons or samples, six from each of two replications. Means were separated using Fisher's Protected LSD at the 0.05 probability level. Entries with a common letter are not significantly different.

TABLE 2

Mean percent establishment of 'DALSA 1618' and tested cultivars across five NTEP locations after planting in the summer of 2016.
Establishment

| | Dallas, TX | | | College Station, TX | |
|---|---|---|---|---|---|
| Genotype | Sep 16 | Nov-16 | Jun-17 | Aug-16 | Oct-16 |
| | | | % | | |
| 'DALSA 1618' | 55.3 | 80.0 | 91.7 | 20.0 | 58.3 |
| 'CitraBlue ®' | 25.7 | 65.0 | 85.0 | 23.3 | 53.3 |

TABLE 2-continued

Mean percent establishment of 'DALSA 1618' and tested cultivars across five NTEP locations after planting in the summer of 2016.
Establishment

| | | | | | |
|---|---|---|---|---|---|
| 'Floratam' | 35.7 | 86.7 | 90.0 | 18.3 | 66.7 |
| 'Palmetto ®' | 32.7 | 68.3 | 81.7 | 18.3 | 66.7 |
| 'Raleigh' | 44.7 | 85.0 | 95.0 | 21.7 | 50.0 |
| LSD* | 15.6 | 16.8 | 15.5 | 9.8 | 23.3 |

| | College Station, TX | Starkville, MS | | | Auburn, AL |
|---|---|---|---|---|---|
| Genotype | Nov-16 | Aug-16 | Sep-16 | Nov-16 | Jul-16 |
| | | | % | | |
| 'DALSA 1618' | 93.3 | 50.0 | 80.0 | 92.3 | 10.0 |
| 'CitraBlue ®' | 75.0 | 36.7 | 68.3 | 90.0 | 5.3 |
| 'Floratam' | 94.7 | 36.7 | 65.0 | 86.3 | 4.3 |
| 'Palmetto ®' | 93.0 | 43.3 | 75.0 | 96.0 | 2.7 |
| 'Raleigh' | 93.3 | 43.3 | 71.7 | 89.3 | 3.7 |
| LSD* | 13.3 | 19.0 | 16.3 | 16.1 | 6.2 |

| | Auburn, AL | | 'Raleigh', NC | | |
|---|---|---|---|---|---|
| Genotype | Sep-16 | Oct-16 | Oct-16 | May-17 | Aug-17 |
| | | | % | | |
| 'DALSA 1618' | 40.0 | 60.0 | 60.0 | 70.0 | 97.7 |
| 'CitraBlue ®' | 55.0 | 68.3 | 51.7 | 28.3 | 84.0 |
| 'Floratam' | 51.7 | 68.3 | 56.7 | 68.3 | 95.3 |
| 'Palmetto ®' | 50.0 | 68.3 | 51.7 | 76.7 | 97.7 |
| 'Raleigh' | 55.0 | 68.3 | 68.3 | 95.0 | 99.0 |
| LSD* | 30.1 | 22.6 | 10.5 | 14.3 | 6.9 |

*Means placed in the top statistical group among 27 genotypes according to Fisher's protected LSD at the 0.05 probability level.

TABLE 3

Turfgrass quality of 'DALSA 1618' and tested cultivars in the 2016 NTEP along latitudes 32 and 33.

| | Turfgrass Quality | | | | |
|---|---|---|---|---|---|
| | Dallas, TX | | | | Starkville, MS |
| Genotype | '17 | '18 | '19 | '20 | '17 |
| | | | 1 to 9 | | |
| 'DALSA 1618' | 6.8 | 8.2 | 7.6 | 7.3 | 6.4 |
| 'CitraBlue ®' | 6.0 | 7.4 | 6.4 | 5.5 | 5.8 |
| 'Floratam' | 5.6 | 6.3 | 5.7 | 5.7 | 5.8 |
| 'Palmetto ®' | 5.8 | 7.7 | 7.0 | 6.4 | 6.3 |
| 'Raleigh' | 5.7 | 7.2 | 6.8 | 5.6 | 6.4 |
| LSD* | 0.9 | 0.9 | 1.3 | 1.1 | 0.9 |

| | Turfgrass Quality | | | | |
|---|---|---|---|---|---|
| | Starkville, MS | | | Auburn, AL | |
| Genotype | '18 | '19 | '20 | '17 | '18 |
| | | | 1 to 9 | | |
| 'DALSA 1618' | 5.4 | 5.7 | 5.2 | 7.3 | 7.1 |
| 'CitraBlue ®' | 5.2 | 6.2 | 5.2 | 5.5 | 5.4 |
| 'Floratam' | 4.1 | 5.1 | 4.8 | 5.8 | 5.3 |
| 'Palmetto ®' | 6.0 | 5.7 | 5.6 | 5.8 | 5.2 |
| 'Raleigh' | 5.6 | 5.4 | 5.7 | 5.0 | 5.0 |
| LSD* | 0.9 | 1.3 | 1.1 | 0.9 | 0.9 |

TABLE 3-continued

Turfgrass quality of 'DALSA 1618' and tested cultivars in the 2016 NTEP along latitudes 32 and 33.

| | Turfgrass Quality | | | | |
|---|---|---|---|---|---|
| | Auburn, AL | | Griffin, GA | | |
| Genotype | '19 | '20 | '17 | '18 | '20 |
| | 1 to 9 | | | | |
| 'DALSA 1618' | 7.4 | 7.0 | 5.9 | 5.7 | 6.6 |
| 'CitraBlue ®' | 6.1 | 6.0 | 5.5 | 6.0 | 6.7 |
| 'Floratam' | 5.0 | 5.3 | 5.4 | 5.8 | 6.4 |
| 'Palmetto ®' | 6.7 | 4.9 | 6.0 | 6.0 | 6.3 |
| 'Raleigh' | 5.6 | 3.9 | 6.3 | 6.1 | 6.1 |
| LSD* | 1.3 | 1.1 | 0.9 | 0.9 | 1.1 |

*Means placed in the top statistical group among 27 genotypes according to Fisher's protected LSD at the 0.05 probability level.

TABLE 4

Turfgrass quality of 'DALSA 1618' and tested cultivars in the 2016 NTEP along coastal areas.

| | Turfgrass Quality | | | | | | | | | | |
|---|---|---|---|---|---|---|---|---|---|---|---|
| | 'Raleigh', NC | | | | Jay, FL | | | | Ft. Lauderdale, FL | | |
| Genotype | '17 | '18 | '19 | '20 | '17 | '18 | '19 | '20 | '18 | '19 | '20 |
| | 1 to 9 | | | | | | | | | | |
| 'DALSA 1618' | 4.6 | 5.9 | 6.1 | 6.5 | 6.7 | 6.3 | 6.4 | 6.7 | 7.2 | 6.4 | 6.5 |
| 'CitraBlue ®' | 3.5 | 6.7 | 4.8 | 7.3 | 6.5 | 5.8 | 7.0 | 7.1 | 8.1 | 8.3 | 7.8 |
| 'Floratam' | 4.5 | 3.1 | 4.2 | 5.3 | 5.9 | 4.8 | 5.8 | 5.7 | 6.8 | 6.7 | 6.5 |
| 'Palmetto ®' | 5.7 | 5.9 | 5.5 | 6.6 | 5.9 | 5.8 | 6.5 | 5.7 | 7.0 | 6.9 | 6.4 |
| 'Raleigh' | 5.7 | 6.2 | 5.3 | 6.4 | 5.9 | 5.8 | 6.1 | 4.9 | 6.8 | 6.4 | 6.4 |
| LSD* | 0.9 | 0.9 | 1.3 | 1.1 | 0.9 | 0.9 | 1.3 | 1.1 | 0.9 | 1.3 | 1.1 |

*Means placed in the top statistical group among 27 genotypes according to Fisher's protected LSD at the 0.05 probability level.

TABLE 5

Turfgrass quality of 'DALSA 1618' and tested cultivars in the 2016 NTEP ancillary trials along coastal areas.

| | Turfgrass Quality | | | | | | | | |
|---|---|---|---|---|---|---|---|---|---|
| | Ft. Lauderdale, FL (low fertilizer) | | | College Station, TX (drought) | | | | Citra, FL (chinch bug) | |
| Genotype | '18 | '19 | '20 | '17 | '18 | '19 | '20 | '17 | '18 |
| | 1 to 9 | | | | | | | | |
| 'DALSA 1618' | 7.1 | 5.7 | 5.8 | 6.5 | 6.9 | 6.6 | 6.7 | 7.7 | 8.0 |
| CitraBlue ®' | 7.8 | 8.4 | 7.7 | 6.1 | 6.1 | 4.8 | 5.4 | 7.3 | 7.9 |
| 'Floratam' | 6.5 | 6.5 | 6.2 | 6.5 | 5.7 | 5.0 | 6.3 | 6.3 | 6.8 |
| 'Palmetto ®' | 6.8 | 6.9 | 6.7 | 6.2 | 6.3 | 5.8 | 6.5 | 7.4 | 7.3 |
| 'Raleigh' | 6.5 | 6.2 | 6.0 | 6.3 | 5.9 | 5.2 | 5.6 | 7.5 | 6.8 |
| LSD* | 0.3 | 1.2 | 1.0 | 0.9 | 0.9 | 1.5 | 1.4 | 0.5 | 0.6 |

*Means placed in the top statistical group among 27 genotypes according to Fisher's protected LSD at the 0.05 probability level.

TABLE 6

Spring greenup of 'DALSA 1618' and tested cultivars in the 2016 NTEP along latitudes 32 and 33.

| | Spring Greenup | | | | | | | |
|---|---|---|---|---|---|---|---|---|
| | Dallas, TX | | | | Starkville, MS | | | |
| Genotype | '17 | '18 | '19 | '20 | '17 | '18 | '19 | '20 |
| | 1 to 9 | | | | | | | |
| 'DALSA 1618' | 3.0 | 2.3 | 3.3 | 4.0 | 4.7 | 2.0 | 4.7 | 4.0 |
| 'CitraBlue ®' | 2.0 | 2.0 | 2.0 | 2.0 | 3.3 | 1.3 | 3.7 | 3.0 |
| 'Floratam' | 2.0 | 1.0 | 2.0 | 2.0 | 3.3 | 1.0 | 3.3 | 2.3 |
| 'Palmetto ®' | 2.3 | 3.7 | 3.3 | 5.7 | 6.3 | 3.0 | 5.0 | 5.0 |
| 'Raleigh' | 2.3 | 2.3 | 3.0 | 5.0 | 5.3 | 3.3 | 4.7 | 5.0 |
| LSD* | 0.8 | 0.8 | 0.8 | 1.3 | 0.9 | 0.8 | 1.0 | 0.9 |

| | Spring Greenup | | | | |
|---|---|---|---|---|---|
| | Auburn, Al | | | Griffin, GA | |
| Genotype | '18 | '19 | '20 | '17 | '18 |
| | 1 to 9 | | | | |
| 'DALSA 1618' | 3.7 | 6.0 | 2.0 | 4.7 | 6.3 |
| 'CitraBlue ®' | 2.0 | 5.3 | 2.0 | 3.0 | 6.3 |
| 'Floratam' | 2.3 | 3.0 | 2.0 | 4.0 | 5.3 |
| 'Palmetto ®' | 3.7 | 6.7 | 2.0 | 3.3 | 5.3 |
| 'Raleigh' | 4.0 | 7.0 | 1.7 | 3.3 | 6.7 |
| LSD* | 1.1 | 2.2 | 0.9 | 1.5 | 1.2 |

*Means placed in the top statistical group among 27 genotypes according to Fisher's protected LSD at the 0.05 probability level.

TABLE 7

Spring greenup of 'DALSA 1618' and tested cultivars in the 2016 NTEP along coastal areas.

| | Spring Greenup | | | | | | | | | |
|---|---|---|---|---|---|---|---|---|---|---|
| | 'Raleigh', NC | | | Jay, FL | | | | Ft. Lauderdale, FL | | |
| Genotype | '18 | '19 | '20 | '17 | '18 | '19 | '20 | '18 | '19 | '20 |
| | 1 to 9 | | | | | | | | | |
| 'DALSA 1618' | 3.0 | 4.7 | 6.0 | 7.3 | 5.0 | 4.0 | 7.3 | 8.3 | 8.3 | 8.3 |
| 'CitraBlue ®' | 2.3 | 3.3 | 3.0 | 7.7 | 4.0 | 3.7 | 8.0 | 8.3 | 8.3 | 8.3 |
| 'Floratam' | 1.0 | 2.0 | 3.3 | 7.7 | 3.0 | 2.0 | 6.3 | 7.0 | 7.0 | 7.0 |
| 'Palmetto ®' | 4.0 | 4.3 | 5.3 | 5.7 | 7.3 | 4.0 | 5.7 | 7.0 | 7.0 | 7.0 |
| 'Raleigh' | 5.7 | 5.3 | 6.0 | 7.0 | 5.0 | 2.3 | 4.7 | 6.7 | 6.7 | 6.7 |
| LSD* | 0.9 | 1.4 | 1.5 | 1.3 | 3.2 | 1.2 | 1.2 | 0.8 | 0.8 | 0.8 |

*Means placed in the top statistical group among 27 genotypes according to Fisher's protected LSD at the 0.05 probability level.

TABLE 8

Spring greenup of 'DALSA 1618' and tested cultivars in the 2016 NTEP ancillary trials along coastal areas.

| | Spring Greenup | | | | | | | | |
|---|---|---|---|---|---|---|---|---|---|
| | Ft. Lauderdale, FL (low fertilizer) | | | College Station, TX (drought) | | | | Citra, FL (Chinch bug) | |
| Genotype | '18 | '19 | '20 | '17 | '18 | '19 | '20 | '17 | '18 |
| | 1 to 9 | | | | | | | | |
| 'DALSA 1618' | 8.3 | 8.3 | 8.3 | 5.7 | 5.3 | 5.7 | 5.7 | 7.0 | 7.0 |
| 'CitraBlue ®' | 8.3 | 8.3 | 8.3 | 6.0 | 4.7 | 4.7 | 5.0 | 7.0 | 6.7 |
| 'Floratam' | 6.7 | 6.7 | 6.7 | 5.7 | 5.7 | 4.0 | 4.3 | 6.7 | 5.0 |

TABLE 8-continued

Spring greenup of 'DALSA 1618' and tested cultivars in the 2016 NTEP ancillary trials along coastal areas.

| | Spring Greenup | | | | | | | | |
|---|---|---|---|---|---|---|---|---|---|
| | Ft. Lauderdale, FL (low fertilizer) | | | College Station, TX (drought) | | | | Citra, FL (Chinch bug) | |
| Genotype | '18 | '19 | '20 | '17 | '18 | '19 | '20 | '17 | '18 |
| 'Palmetto ®' | 6.7 | 6.7 | 6.7 | 7.0 | 7.3 | 5.7 | 6.0 | 6.7 | 4.7 |
| 'Raleigh' | 6.3 | 6.3 | 6.3 | 6.7 | 7.7 | 5.3 | 5.7 | 6.3 | 4.3 |
| LSD* | 1.0 | 1.0 | 1.0 | 1.1 | 1.7 | 1.4 | 1.4 | 0.9 | 1.1 |

*Means placed in the top statistical group among 27 genotypes according to Fisher's protected LSD at the 0.05 probability level.

TABLE 9

Winter survival of 'DALSA 1618' and tested cultivars in 2016 NTEP locations.

| | Living Cover (spring) | | | | | |
|---|---|---|---|---|---|---|
| | Dallas, TX | | Starkville, MS | | | |
| Genotype | '17 | '20 | '17 | '18 | '19 | '20 |
| | | | % | | | |
| 'DALSA 1618' | 58.3 | 51.7 | 75.0 | 38.3 | 85.0 | 53.3 |
| 'CitraBlue ®' | 38.3 | 11.7 | 60.0 | 40.0 | 70.0 | 36.7 |
| 'Floratam' | 55.0 | 5.0 | 45.0 | 8.3 | 63.3 | 30.0 |
| 'Palmetto ®' | 51.7 | 70.0 | 92.3 | 41.7 | 85.0 | 83.3 |
| 'Raleigh' | 65.0 | 60.0 | 85.0 | 53.3 | 76.7 | 80.0 |
| LSD* | 17.3 | 22.9 | 14.2 | 15.8 | 13.8 | 21.7 |

| | Living Cover (spring) | | | | | Winterkill |
|---|---|---|---|---|---|---|
| | 'Raleigh', NC | | | Citra, FL (chinch bug) | | Dallas, TX |
| Genotype | '17 | '18 | '19 | '17 | '18 | '18 |
| | | | % | | | |
| 'DALSA 1618' | 56.7 | 65.0 | 75.0 | 76.7 | 98.3 | 16.7 |
| 'CitraBlue ®' | 20.0 | 65.0 | 55.0 | 58.3 | 98.3 | 13.3 |
| 'Floratam' | 56.7 | 10.0 | 40.0 | 48.3 | 98.7 | 66.7 |
| 'Palmetto ®' | 68.3 | 90.7 | 73.3 | 66.7 | 99.0 | 15.0 |
| 'Raleigh' | 78.3 | 91.3 | 88.3 | 75.0 | 99.0 | 20.0 |
| LSD* | 15.5 | 22.5 | 27.6 | 17.0 | 4.3 | 21.1 |

| | Winterkill | | |
|---|---|---|---|
| Genotype | Dallas, TX '19 | Auburn, AL '19 | Jay, FL '19 |
| | % | 1 to 9 | |
| 'DALSA 1618' | 20.0 | 7.3 | 5.0 |
| 'CitraBlue ®' | 43.3 | 7.7 | 4.0 |
| 'Floratam' | 69.2 | 5.0 | 4.3 |
| 'Palmetto ®' | 25.8 | 8.3 | 7.0 |
| 'Raleigh' | 32.5 | 8.0 | 7.0 |
| LSD* | 21.9 | 2.8 | 2.3 |

*Means placed in the top statistical group among 27 genotypes according to Fisher's protected LSD at the 0.05 probability level.

TABLE 10

Genetic color and shoot density of 'DALSA 1618' and tested cultivars across standard and ancillary NTEP locations.

| | Genetic Colort | | | Shoot Density‡ | |
|---|---|---|---|---|---|
| | | | | Standard locations mean | |
| Genotype | Standard locations mean | Low fertilizer | Drought | Spring | Summer |
| | | | 1 to 9 | | |
| 'DALSA 1618' | 6.7 | 7.7 | 6.8 | 6.6 | 7.6 |
| 'CitraBlue ®' | 7.6 | 8.3 | 6.2 | 6.7 | 7.5 |
| 'Floratam' | 6.3 | 7.7 | 6.8 | 5.4 | 6.3 |
| 'Palmetto ®' | 6.2 | 8.0 | 6.3 | 6.0 | 6.5 |
| 'Raleigh' | 6.1 | 8.0 | 6.1 | 5.8 | 6.4 |
| LSD* | 0.6 | 0.4 | 0.5 | 1.2 | 0.8 |

| | Shoot Density‡ | | | |
|---|---|---|---|---|
| | Standard locations mean | Low fertilizer | | |
| Genotype | Fall | Spring | Summer | Fall |
| | | | 1 to 9 | |
| 'DALSA 1618' | 7.1 | 6.3 | 8.7 | 7.0 |
| 'CitraBlue ®' | 8.0 | 8.3 | 9.0 | 7.9 |
| 'Floratam' | 6.5 | 6.0 | 7.3 | 6.6 |
| 'Palmetto ®' | 7.1 | 7.3 | 7.3 | 7.4 |
| 'Raleigh' | 6.6 | 6.0 | 7.0 | 6.3 |
| LSD* | 0.9 | 1.7 | 1.6 | 0.7 |

*Means placed in the top statistical group among 27 genotypes according to Fisher's protected LSD at the 0.05 probability level.
†Mean genetic color was rated at six standard NTEP locations (Dallas, TX; Starkville, MS; Auburn, AL; Griffin, GA; Jay, FL; and Ft. Lauderdale, FL) and two ancillary locations (Ft. Lauderdale, FL (low fertilizer); and College Station, TX (drought).
‡Mean shoot density was rated in the spring (Jay, FL and Ft. Lauderdale, FL), summer (Dallas, TX; Jay, FL; and Ft. Lauderdale, FL), and fall (Jay, FL and Ft. Lauderdale, FL) under standard and low fertilizer trial conditions (Ft. Lauderdale, FL).

TABLE 11

Seasonal color retention of 'DALSA 1618' and tested cultivars at 2016 NTEP locations.

| | | | | Winter Color‡ Standard locations | |
|---|---|---|---|---|---|
| | Fall Color† | | | Dallas, | Jay, |
| Genotype | Sept | Oct | Nov | TX | FL |
| | | | 1 to 9 | | |
| 'DALSA 1618' | 6.7 | 6.7 | 5.1 | 5.3 | 4.0 |
| 'CitraBlue ®' | 7.7 | 7.3 | 6.9 | 4.0 | 2.3 |
| 'Floratam' | 6.8 | 6.4 | 5.3 | 3.3 | 2.3 |
| 'Palmetto ®' | 6.2 | 6.4 | 4.3 | 5.3 | 3.7 |
| 'Raleigh' | 6.0 | 6.2 | 3.7 | 4.3 | 3.7 |
| LSD* | 0.8 | 0.7 | 1.2 | 1.2 | 1.0 |

| | Winter Color‡ | | | |
|---|---|---|---|---|
| | Standard locations | Ancillary locations | | |
| Genotype | Ft. Lauderdale, FL | Ft. Lauderdale, FL | College Station, TX | Citra, FL |
| | | 1 to 9 | | |
| 'DALSA 1618' | 7.1 | 6.6 | 4.8 | 5.7 |
| 'CitraBlue ®' | 8.3 | 8.1 | 5.3 | 5.3 |

TABLE 11-continued

Seasonal color retention of 'DALSA 1618' and tested cultivars at 2016 NTEP locations.

| | | | | |
|---|---|---|---|---|
| 'Floratam' | 7.2 | 6.9 | 5.1 | 4.3 |
| 'Palmetto ®' | 7.4 | 7.3 | 4.8 | 5.7 |
| 'Raleigh' | 7.0 | 6.7 | 4.4 | 5.3 |
| LSD* | 1.3 | 0.9 | 3.0 | 0.8 |

*Means placed in the top statistical group among 27 genotypes according to Fisher's protected LSD at the 0.05 probability level.

†Mean fall color retention was rated at standard NTEP locations in September (13 times between Auburn, AL; Griffin, GA; Jay, FL; and Ft. Lauderdale, FL), October (10 times between Dallas, TX; Griffin, GA; and Jay, FL), and November (6 times between Dallas, TX; Auburn, AL; Jay, FL; and 'Raleigh', NC).

‡Mean winter color retention was rated at three standard NTEP locations (8 times between Dallas, TX; Jay, FL; and Ft. Lauderdale, FL) and three ancillary locations (5 times between Ft. Lauderdale, FL (low fertilizer); College Station, TX (drought); and Citra, FL (chinch bug).

TABLE 12

Resistance to large patch and gray leaf spot of 'DALSA 1618' and cultivars in 2016 NTEP trial.

| | Large Patch† | | | |
|---|---|---|---|---|
| | Standard locations | | | Ancillary |
| Genotype | Dallas, TX | Starkville, MS | 'Raleigh', NC | location Citra, FL |
| | 1 to 9 | | | |
| 'DALSA 1618' | 9.0 | 7.0 | 7.0 | 8.5 |
| 'CitraBlue ®' | 9.0 | 8.0 | 9.0 | 8.3 |
| 'Floratam' | 9.0 | 8.0 | 9.0 | 8.7 |
| 'Palmetto ®' | 8.3 | 7.7 | 8.3 | 7.0 |
| 'Raleigh' | 8.7 | 7.7 | 8.7 | 8.2 |
| LSD* | 1.7 | 2.3 | 3.2 | 1.4 |

| | Gray Leaf Spot‡ Standard locations | | | |
|---|---|---|---|---|
| Genotype | Dallas, TX | Starkville, MS | 'Raleigh', NC | Ft. Lauderdale, FL |
| | 1 to 9 | | | |
| 'DALSA 1618' | 7.3 | 7.7 | 7.4 | 7.9 |
| 'CitraBlue ®' | 6.0 | 7.3 | 8.0 | 9.0 |
| 'Floratam' | 6.6 | 3.7 | 5.1 | 8.3 |
| 'Palmetto ®' | 6.8 | 4.3 | 5.1 | 8.6 |
| 'Raleigh' | 6.4 | 3.3 | 4.8 | 7.3 |
| LSD* | 1.4 | 1.3 | 1.7 | 2.8 |

| | Gray Leaf Spot‡ Ancillary locations | |
|---|---|---|
| Genotype | Ft. Lauderdale, FL | Citra, FL |
| | 1 to 9 | |
| 'DALSA 1618' | 6.4 | 9.0 |
| 'CitraBlue ®' | 8.9 | 7.3 |
| 'Floratam' | 8.3 | 4.5 |
| 'Palmetto ®' | 8.6 | 8.5 |

TABLE 12-continued

Resistance to large patch and gray leaf spot of 'DALSA 1618' and cultivars in 2016 NTEP trial.

| | | |
|---|---|---|
| 'Raleigh' | 7.4 | 9.0 |
| LSD* | 2.3 | 1.9 |

*Means placed in the top statistical group among 27 genotypes according to Fisher's protected LSD at the 0.05 probability level.

†Large patch was rated on a 1 to 9 scale (1 = completely susceptible, 9 = no disease present). Ratings occurred in 2018 in Dallas, TX, and in 2020 in Starkville, MS. Large patch was rated in September and November 2020 in 'Raleigh', NC, and once in each 2017 and 2018 in Citra, FL (chinch bug).

‡Gray leaf spot was rated frequently but only in a few locations on a 1 to 9 scale (1 = completely susceptible, 9 = no disease present). In Dallas, TX, GLS was rated once in August 2016, April 2017, and September 2017. It was only rated once in Starkville, MS in 2017, and in September and October 2017 and in August and September 2018 in 'Raleigh', NC. Under the standard and low fertilizer trials in Ft. Lauderdale, FL, ratings occurred once in each 2018, 2019, and 2020. Disease was rated once in 2017 and 2018 in Citra, FL (chinch bug).

TABLE 13

Drought tolerance traits evaluated in College Station, TX as part of the 2016 NTEP.

| Genotype | Wilting† | Dormancy‡ 1 to 9 | Recovery§ |
|---|---|---|---|
| DALSA1618 | 6.1 | 3.7 | 7.0 |
| 'CitraBlue ®' | 5.5 | 3.0 | 6.6 |
| 'Floratam' | 5.4 | 2.3 | 6.0 |
| 'Palmetto ®' | 4.6 | 1.3 | 5.5 |
| 'Raleigh' | 4.5 | 1.5 | 5.2 |
| LSD* | 0.7 | 1.6 | 1.6 |

*Means were in the top statistical group among all 27 genotypes according to Fisher's Protected LSD at the 0.05 probability level.

†Wilting is the average of four ratings collected once in each 2017, 2018, 2019, and 2020.

‡Dormancy was rated once in 2018.

§Recovery is the average of two ratings collected once after each of the 2017 and 2018 drought periods.

TABLE 14

Performance of 'DALSA 1618' compared to 'Floratam' under Approach "A" modified irrigation in College Station, TX.

| Irrigation Level | Genotype | Percent Green Cover Apr. 26, 2017 | May 25, 2017 | Jun. 1, 2018 | Jul. 5, 2018 | Aug. 3, 2018 |
|---|---|---|---|---|---|---|
| Unirrigated | 'DALSA 1618' | 71.7 | 78.3 | 94.1 | 82.9 | 82.9 |
| | 'Floratam' | 75.0 | 83.3 | 97.6 | 79.5 | 69.0 |
| Once per month | 'DALSA 1618' | 81.7 | 81.7 | 81.1 | 90.2 | 68.0 |
| | 'Floratam' | 61.7 | 76.7 | 92.1 | 93.2 | 64.4 |
| Once every two weeks | 'DALSA 1618' | 73.3 | 80.0 | 79.1 | 71.3 | 60.2 |
| | 'Floratam' | 73.3 | 86.7 | 89.8 | 76.5 | 51.8 |
| Once weekly | 'DALSA 1618' | 86.7 a‡ | 83.3 | 93.8 a | 75.2 | 40.0 |
| | 'Floratam' | 56.7 b | 71.7 | 82.7 b | 78.3 | 54.6 |
| Twice weekly | 'DALSA 1618' | 80.0 | 81.7 | 82.5 | 80.9 | 61.8 |
| | 'Florata' | 63.3 | 80.0 | 94.8 | 95.2 | 82.9 |

| Irrigation Level | Genotype | Quality† 2017 | 2018 |
|---|---|---|---|
| Unirrigated | 'DALSA 1618' | 6.3 | 5.1 |
| | 'Floratam' | 6.4 | 4.7 |
| Once per month | 'DALSA 1618' | 6.3 | 5.3 |
| | 'Floratam' | 6.3 | 4.9 |

TABLE 14-continued

Performance of 'DALSA 1618' compared to 'Floratam' under Approach "A" modified irrigation in College Station, TX.

| | | | |
|---|---|---|---|
| Once every two weeks | 'DALSA 1618' | 6.9 | 6.3 a |
| | 'Floratam' | 6.6 | 5.5 b |
| Once weekly | 'DALSA 1618' | 7.0 | 6.8 a |
| | 'Floratam' | 6.9 | 5.9 b |
| Twice weekly | 'DALSA 1618' | 7.2 | 6.7 |
| | 'Florata' | 7.0 | 6.4 |

†Quality means in 2017 represent three replications and five rating dates from 24 July through 28 September. Means in 2018 represent three replications and nine rating dates from 21 May through 2 October.
‡Entries with a common letter are not significantly different.

TABLE 15

Performance of 'DALSA 1618' compared to 'Floratam' and 'Palmetto ®' under Approach "B" modified irrigation in College Station, TX. Irrigation was applied to promote establishment in 2016, once per week in 2017, and once every 14 days in 2018.

| | Percent Green Cover | | | | | | |
|---|---|---|---|---|---|---|---|
| | Apr. 20, | May 18, | Jun. 1, | Jul. 9, | Aug. 13, | Quality† | |
| Genotype | 2017 | 2017 | 2018 | 2018 | 2018 | 2017 | 2018 |
| 'DALSA 1618' | 83.3 | 100.0 | 91.9 | 79.1 | 38.9 | 7.0 | 4.9 a |
| 'Floratam' | 86.7 | 100.0 | 90.9 | 74.6 | 40.5 | 6.8 | 5.0 a |
| 'Palmetto ®' | 70.0 | 100.0 | 86.2 | 62.9 | 27.3 | 6.2 | 4.0 b |
| LSD* | NS | NS | NS | NS | NS | NS | 0.8 |

†Quality means were separated by year due to different irrigation treatments. Means are the product of four rating dates in 2017 and eight dates in 2018.
*Means are statistically different from other cultivars at the 0.05 probability level. Entries with a common letter are not significantly different.

TABLE 16

Performance of 'DALSA 1618' and commercial cultivars under Approach "B" in Dallas, TX. No supplemental irrigation was applied during the summer months in 2017, 2018, or 2019.

| | Quality† | | | | | |
|---|---|---|---|---|---|---|
| | Normal | | | | | Recov- |
| Genotype | '16 | '17 | '18 | '19 | Drought | ery |
| | 1 to 9 | | | | | |
| 'DALSA 1618' | 6.3 | 7.1 a | 6.0 a | 6.6 a | 4.7 a | 6.4 a |
| 'Floratam' | 4.7 | 4.9 b | 3.3 b | 3.9 b | 3.4 b | 4.7 b |
| 'Palmetto ®' | 4.7 | 5.2 b | 2.3 b | 1.6 c | 1.8 c | 2.8 c |
| 'Raleigh' | 5.0 | 5.1 b | 3.0 b | 3.8 b | 2.2 c | 3.3 c |
| LSD* | NS | 0.8 | 1.3 | 1.3 | 0.5 | 1.0 |

| Genotype | Fall Color‡ | Spring Green-up§ | Gray Leaf Spot¶ |
|---|---|---|---|
| | 1 to 9 | | |
| 'DALSA 1618' | 6.2 a | 7.8 a | 7.3 a |
| 'Floratam' | 3.5 b | 2.8 b | 3.7 b |
| 'Palmetto ®' | 1.5 c | 2.0 b | 2.0 c |

TABLE 16-continued

Performance of 'DALSA 1618' and commercial cultivars under Approach "B" in Dallas, TX. No supplemental irrigation was applied during the summer months in 2017, 2018, or 2019.

| | | | |
|---|---|---|---|
| 'Raleigh' | 2.3 c | 2.8 b | 2.0 c |
| LSD* | 1.1 | 1.0 | 1.5 |

*Means are statistically different from other cultivars at the 0.05 probability level. Entries with a common letter are not significantly different.

†Quality was analyzed with entry, year, and entry by year as factors for each well-watered and drought periods. Entry by year analysis was significant for normal quality but not for drought or recovery, so means are presented separately by year for normal quality and combined within drought and recovery treatments. Normal quality is the mean of one rating in 2016, three ratings in 2017, and one rating in each 2018 and 2019. Drought quality is the average of seven rating dates and recovery quality is the average of three ratings.

‡Fall color retention was analyzed with entry, year, and entry by year as factors. Entry by year was not significant so means were combined from 2017 and 2018.

§Spring greenup was analyzed with entry, year, and entry by year as factors. Entry by year was not significant so means were combined from 2017, 2018, and 2019.

¶Gray leaf spot was rated on 2 Oct. 2018.

TABLE 17

Digital percent green cover of 'DALSA 1618', 'Amerishade ®', 'Floratam', 'Palmetto ®', and 'Raleigh' under 63% shade in Dallas, TX.

| | Days after planting Year 1 (2017) | | | | |
|---|---|---|---|---|---|
| Genotype | 22 | 33 | 47 | 61 | 78 |
| 'DALSA 1618' | 17.4 | 22.0 | 25.6 | 36.9 | 44.1 |
| 'Amerishade ®' | 17.2 | 22.0 | 24.6 | 32.1 | 29.7 |
| 'Floratam' | 12.6 | 13.0 | 13.4 | 18.1 | 23.4 |
| 'Palmetto ®' | 15.5 | 18.0 | 19.8 | 33.3 | 34.6 |
| 'Raleigh' | 14.0 | 14.8 | 17.9 | 25.6 | 32.2 |
| LSD* | NS | NS | NS | NS | NS |

| | Days after planting Year 2 (2018) | | | |
|---|---|---|---|---|
| Genotype | 345 | 358 | 372 | 384 |
| 'DALSA 1618' | 47.4 a | 59.2 a | 68.3 a | 72.7 a |
| 'Amerishade ®' | 35.7 a | 39.1 a | 54.6 a | 67.1 a |
| 'Floratam' | 1.8 b | 1.7 b | 1.6 b | 1.9 b |
| 'Palmetto ®' | 34.0 a | 44.5 a | 56.9 a | 69.3 a |
| 'Raleigh' | 30.4 a | 38.6 a | 49.4 a | 58.2 a |
| LSD* | 24.5 | 29.9 | 34.9 | 35.3 |

| | Days after planting Year 2 (2018) | |
|---|---|---|
| Genotype | 428 | 400 |
| 'DALSA 1618' | 79.1 a | 80.5 a |
| 'Amerishade ®' | 73.2 a | 75.3 a |
| 'Floratam' | 1.7 b | 1.5 b |
| 'Palmetto ®' | 77.1 a | 77.8 a |
| 'Raleigh' | 69.4 a | 66.9 a |
| LSD* | 14.9 | 22.6 |

*Means were separated by Fisher's protected LSD at the 0.05 probability level if entry was a significant factor. Entries with a common letter are not significantly different.

TABLE 18

Turfgrass performance of 'DALSA 1618', 'Amerishade ®', 'Palmetto ®', and 'Raleigh' under 63% shade in Dallas, TX.

| | Turfgrass Quality† | | | | Plot | Shoot Density‡ | |
|---|---|---|---|---|---|---|---|
| Genotype | '17 | '18 | '19 | '20 | Color‡ | '18 | '19 |
| | | | | 1 to 9 | | | |
| 'DALSA 1618' | 6.5 a | 5.8 a | 7.5 a | 7.0 | 6.1 a | 5.6 ab | 5.4 a |
| 'Amerishade ®' | 6.4 a | 4.7 b | 4.8 c | 4.7 | 6.1 a | 6.1 a | 4.9 a |
| 'Floratam'‡‡ | 4.7 b | — | — | — | — | — | — |
| 'Palmetto ®' | 5.0 b | 5.0 b | 6.5 b | 6.0 | 5.2 b | 5.3 b | 4.9 a |
| 'Raleigh' | 5.9 a | 4.1 b | 4.0 d | 4.3 | 5.2 b | 5.0 b | 3.9 b |
| LSD* | 0.71 | 0.7 | 0.3 | NS | 0.4 | 0.7 | 0.6 |

| | Fall | Spring Green- | Gray Leaf | DER†† | |
|---|---|---|---|---|---|
| Genotype | Color§ | up¶ | Spot# | '17 | '18 |
| | | 1 to 9 | | $mm \cdot d^{-1}$ | |
| 'DALSA 1618' | 5.0 | 4.5 | 5.7 | 1.0 a | 1.0 a |
| 'Amerishade ®' | 3.3 | 2.8 | 4.7 | 0.6 b | 0.8 b |
| 'Floratam'‡‡ | — | — | — | 1.0 a | — |
| 'Palmetto ®' | 4.0 | 3.7 | 5.3 | 0.9 a | 1.1 a |
| 'Raleigh' | 3.7 | 2.7 | 4.3 | 1.0 a | 1.0 a |
| LSD* | NS | NS | NS | 0.2 | 0.1 |

*Means placed in the top statistical group according to Fisher's protected LSD at the 0.05 probability level. Data was analyzed with entry, year, and entry by year as fixed effects and replication as a random effect. If entry by year was significant, data is presented for each year. Entries with a common letter are not significantly different.

†Turfgrass quality is the average of three replications rated every two weeks between August 16 to October 12 in 2017, June 28 to October 4 in 2018, May 15 to August 23 in 2019, and September 20, 2020.

‡Plot color and shoot density are the averages of three replications rated biweekly between August 16 and October 12 in 2017 (5 dates) and June 28 to October 4 in 2018 (8 dates).

§Fall color was rated once on Nov. 15, 2019.

¶Spring greenup is the average between May 16, 2018 and Apr. 23, 2019.

Gray leaf spot susceptibility is the average of ratings on July 26 and October 4 in 2018.

††Leaf lengths were measured from the two longest leaves in each of three replicate plots under moderate shade every two weeks from August 22 to October 6 in 2017 (4 dates), and from June 28 to October 5 in 2018 (8 dates) for a total of 12 collection dates. Mean leaf lengths for each plot were then divided by the number of days since the last mowing event to calculate daily leaf elongation rates (DER, $mm \cdot d^{-1}$). Genotype by year was not a significant effect so means were combined.

‡‡Poor survival did not warrant collecting data from 2018 to 2020.

TABLE 19

Percent establishment of 'DALSA 1618', 'Floratam', and 'Raleigh' Pooled Across College Station and Dallas, TX.

| GENOTYPE | 3WAP† | 4WAP | 6WAP | 8WAP |
|---|---|---|---|---|
| | | % | | |
| 'DALSA 1618' | 24.75 a‡ | 32.95 a | 44.50 a | 67.75 a |
| 'FLORATAM' | 23.25 ab | 28.75 ab | 34.00 b | 47.50 a |
| 'RALEIGH' | 21.50 b | 26.75 b | 33.75 b | 43.75 a |

| GENOTYPE | 10WAP | 36WAP | AVG. |
|---|---|---|---|
| | | % | |
| 'DALSA 1618' | 81.00 a | 88.25 a | 56.84 a |
| 'FLORATAM' | 61.25 b | 63.50 b | 43.04 b |
| 'RALEIGH' | 57.55 b | 63.00 b | 41.05 b |

†WAP, weeks after planting

‡Entries within columns with a common letter are not significantly different at the 0.05 probability level.

TABLE 20

Sod tensile strength (STS) of 'DALSA' 1618, 'Raleigh', and 'Floratam' in College Station and Dallas, TX.

| | Sod Tensile Strength ($kg \cdot dm^2$) | |
|---|---|---|
| Genotype | Dallas | College Station |
| 'DALSA 1618' | 108.67 a† | 155.06 a |
| 'Floratam' | 141.96 a | 45.33 b |
| 'Raleigh' | 68.82 a | 52.44 b |

†Entries within columns with a common letter are not significantly different at the 0.05 probability level.

What is claimed is:

1. A new and distinct interploid hybrid variety of St. Augustinegrass named 'DALSA 1618' as shown and described herein.

* * * * *